United States Patent
Taniguchi et al.

(10) Patent No.: US 9,951,312 B2
(45) Date of Patent: Apr. 24, 2018

(54) METHOD FOR PREPARATION OF CARTILAGE CELL

(75) Inventors: Hideki Taniguchi, Kanagawa (JP); Shinji Kobayashi, Kanagawa (JP)

(73) Assignee: Yokohama City University, Kanagawa (JP)

( * ) Notice: Subject to any disclaimer, the term of this patent is extended or adjusted under 35 U.S.C. 154(b) by 564 days.

(21) Appl. No.: 12/524,359

(22) PCT Filed: Jan. 23, 2008

(86) PCT No.: PCT/JP2008/051327
§ 371 (c)(1),
(2), (4) Date: Aug. 27, 2009

(87) PCT Pub. No.: WO2008/091013
PCT Pub. Date: Jul. 31, 2008

(65) Prior Publication Data
US 2009/0324560 A1 Dec. 31, 2009

(30) Foreign Application Priority Data
Jan. 23, 2007 (JP) ................................. 2007-012160

(51) Int. Cl.
*A61K 35/12* (2015.01)
*C12N 5/0797* (2010.01)
(Continued)

(52) U.S. Cl.
CPC ............ *C12N 5/0655* (2013.01); *A61K 35/32* (2013.01); *C12N 2500/25* (2013.01);
(Continued)

(58) Field of Classification Search
CPC .............. C12N 5/0655; C12N 2500/25; C12N 2501/105; C12N 2501/115; C12N 2501/39; A61K 35/32
See application file for complete search history.

(56) References Cited

U.S. PATENT DOCUMENTS 5,919,702 A * 7/1999 Purchio et al. ............... 435/378
2006/0088506 A1   4/2006 Yanaga

FOREIGN PATENT DOCUMENTS

| JP | 11-508358 A | 7/1999 |
| JP | 2003-505143 A | 2/2003 |
| JP | 2006-514839 A | 5/2006 |

OTHER PUBLICATIONS

Dounchis et al., "Chondrogenic Phenotype of perichondrium-Derived Chondroprogenitor Cells is Influenced by Transforming growth factor-Beta 1", Journal of Orthopaedic Research, 1997, vol. 15, No. 6, pp. 803-807.*

(Continued)

*Primary Examiner* — Laura Schuberg
(74) *Attorney, Agent, or Firm* — Morgan, Lewis & Bockius LLP

(57) ABSTRACT

Chondrocytes are prepared from perichondrocytes.
The present invention provides a cell derived from a perichondrial tissue, the cell being capable of differentiating into a chondrocyte. The present invention also provides a method of preparing the above-described cell and a composition comprising the same. A method of preparing a chondrocyte and a medium for use in the method are also provided.

19 Claims, 20 Drawing Sheets
(12 of 20 Drawing Sheet(s) Filed in Color)

(51) Int. Cl.
  A61P 19/00 (2006.01)
  C12N 5/077 (2010.01)
  A61K 35/32 (2015.01)
(52) U.S. Cl.
  CPC .. *C12N 2501/105* (2013.01); *C12N 2501/115* (2013.01); *C12N 2501/39* (2013.01)

(56) References Cited

OTHER PUBLICATIONS

Marlovits et al., "Changes in the ratio of type-I and type-II collagen expression during monolayer culture of human chondrocytes", The Journal of Bone and Joint Surgery [Br], 2004, vol. 86-B, No. 2, pp. 286-295.*
Bulstra et al., "The Potential of Adult Human Perichondrium to Form Hyalin Cartilage In Vitro", Journal of Orthopaedic Research, 1990, vol. 8, pp. 328-335.*
Duynstee et al, "The Dual Role of Perichondrium in cartilage Wound Healing" , Plastic Reconstructive Surgery, 2002, vol. 110, pp. 1073-1079.*
Extended European Search Report issued in the corresponding European patent application No. 08704109.1, 2010 pp. 1-7.
International Search Report for PCT/JP2008/051327, dated Apr. 15, 2008, pp. 1-9.
Ken'ichi Kajitani et al., "Kansetsu Nankotsu Zenso Kessongo ni Shojiru shuhenbu no Kansetsusho Henka ni Taisuri Collagen Gel Naiho Ri Baiyo Nankotsu Saibo Ishokujutsu no Yukosei", The Journal of the Japanese Orthopaedic Association, Vo. 76, No. 8, p. S1075, (Aug. 25, 2002).
Koji Hattori et al., "Saisei Iryo Nyumon Koza 10 Hone Nankotsu—Nankotsu Saisei no Jissai", Regenerative Medicine, (Aug. 1, 2005), vol. 4, No. 3, pp. 430 to 437, 351.
Mitsuo Ochi et al., "Saisei Igaku no Genjo to Tenbo 7 Kansetsu Nankotsu no Saisei", Bio Clin, vol. 15, No. 14, pp. 1119 to 1122, (Dec. 20, 2000), vol. 15, No. 14, pp. 1119 to 1122.
Togo, T. et al., Identification of cartilage progenitor cells in the adult ear perchondrium: utilization for cartilage reconstruction, Lab oratory investigation; a journal of technical methods and pathology, 2006, vol. 86, No. 5, p. 445-457.
Takeshi Togo et al., "Jikai Nankotsumaku ni yoru Jikai Nankotsu Saisei", Dai 14 Kai Japan Society of Plastic and Reconstructive Surgery Kisoi Gakujutsu Shukai Program Shorokushu, (Oct. 14, 2005), p. 83, 57.
Takeshi Togo et al., "Jikai Nankotsumaku ni yoru Jikai Nankotsu Saisei: donor to Shiteno Shishitsu", Dai 37 Kai Japanese Society of Connective Tissue Research Gakujutsu Taikai Shorokushu, (May 26, 2005), p. 52.
Takeshi Togo et al., "Jikai Nankotsumaku ni Okeru Soshiki Kansaibo no Dotei: Nankotsu Saisei eno Oyo", Dai 38 Kai Japanese Society of Connective Tissue Research Gakujutsu taikai Shorokushu, (Apr. 6, 2006) p. 62.
Yusuke Sakaguchi et al., "Nankotsu Saisei ni Yuyo na Saibogen no Kento", Journal of the Eastern Japan Association of Orthopaedics and Traumatology, vol. 17, No. 3, p. 425, (Aug. 23, 2005).
Keita Nishimura, "Katsumaki no Nankotsu Bunkano", Rheumatology, vol. 26, No. 2, pp. 196 to 203, (Aug. 28, 2001).
Park, J. et al., Transgene-activated mesenchymal cells for articular cartilage repair: a comparison of primary bone marrow-, perichondrium/periosteum- and fat-derived cells, The journal of gene medicine, 2006, vol. 8, No. 1, p. 112-125.
Togo, Takeshi et al., "Identification of Cartilage Progenitor Cells in the Adult Ear Perichondrium: Utilization for Cartilage Reconstruction," Laboratory Investigation, vol. 86, pp. 445-457, 2006.
Yanaga, Hiroko et al., "Clinical Application of cultured Autologous Human Auricular chondrocytes with Autologous Serum for Craniofacial or Nasal augmentation and Repair," Plastic and Reconstructive Surgery, vol. 117, No. 6, pp. 2019-2030, May 2006.
Bi, Yanming et al., "Identification of tendon stem-progenitor cells and the role of the extracellular matrix in their niche," Nature Medicine, vol. 13, No. 10, pp. 1219-1227, Oct. 2007.
Dounchis, J. S. et al., "Chondrogenic Phenotype of Perichondrium-Derived Chondroprpgenitor Cells is Influenced by transforming Growth Factor-Beta 1," Journal of Orthopaedic Research, vol. 15, No. 6, pp. 803-807, 1997.
Lee, Myung C. et al., "Transforming Growth Factor Beta One (TGF-β1) Enhancement of the Chondrocytic Phenotype in Aged perichondrial Cells: An In Vitro Study," The Iowa Orthopaedic Journal, vol. 20, pp. 11-16.
Giurea, Alexander et al., "Adhesion of Perichondrial Cells to a Polylactic Acid Scaffold," Journal of Orthopaedic Research, vol. 21, pp. 584-589, 2003.
Facer, S. R. et al., "Rotary Culture Enhances Pre-osteoblast Aggregation and Mineralization," J. Dent. res., vol. 84, No. 6, pp. 542-547, 2005.
Cheng et al., "Immunomagnetic Indirect Positive Sorting of Precartilaginous Stem Cells from Neonatal Rat" Journal of Huazhong University of Science and Technology, Medical Sciences, vol. 26, No. 6, pp. 723-724, 2006.
Bairati et al., "A comparative study of perichondrial tissue in mammalian cartilages" Tissue & Cell, vol. 28, No. 4, pp. 455-468, Aug. 1996.
Kobayashi et al., "Reconstruction of human elastic cartilage by a CD44+ CD90+ stem cell in the ear perichondrium" Proceedings of the National Academy of Sciences, vol. 108, No. 35, pp. 14479-14484, Aug. 30, 2011.
European office action dated Nov. 25, 2011 for corresponding European application 08704109.1 cites the non-patent literature above.
Chinese language office action dated Oct. 19, 2012 and its Japanese and English language translations issued in corresponding Chinese application 200880002777.4.

* cited by examiner

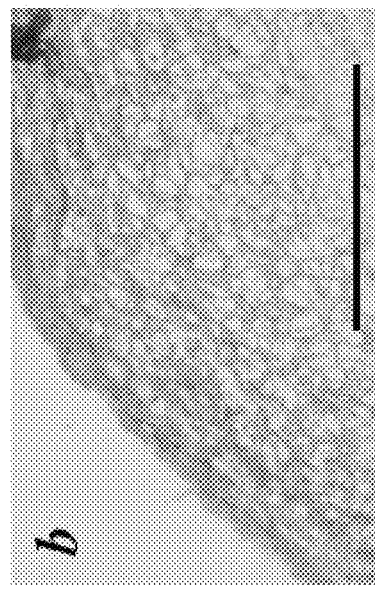
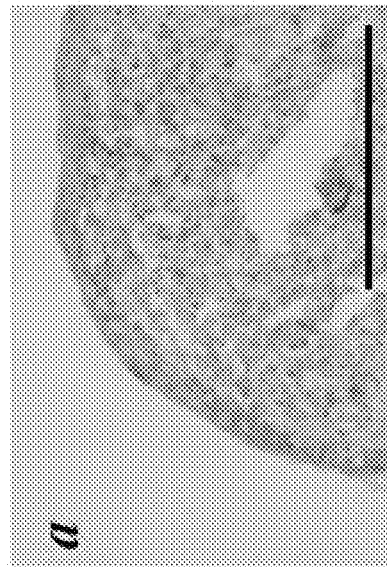
Fig. 2

Fig. 5

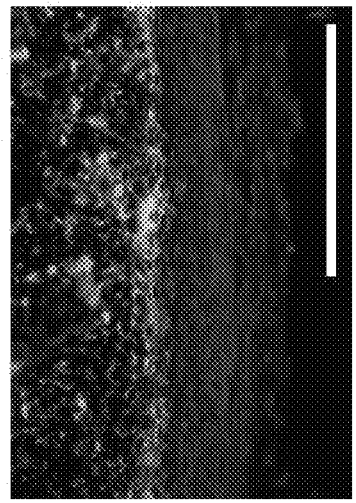
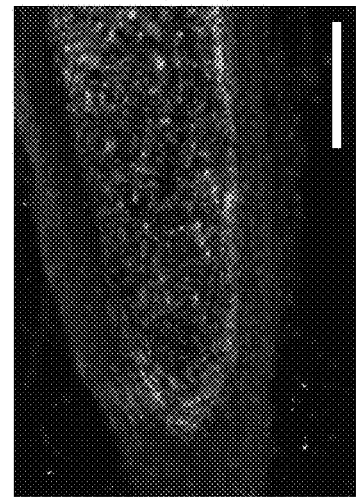
Fig. 9

Fig. 15
A. Induction of Adipogenic Differentiation
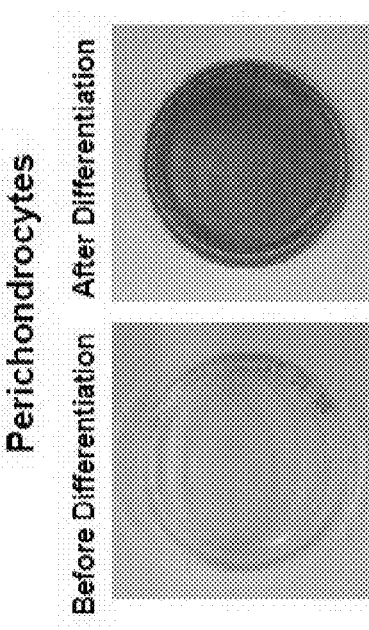
Perichondrocytes
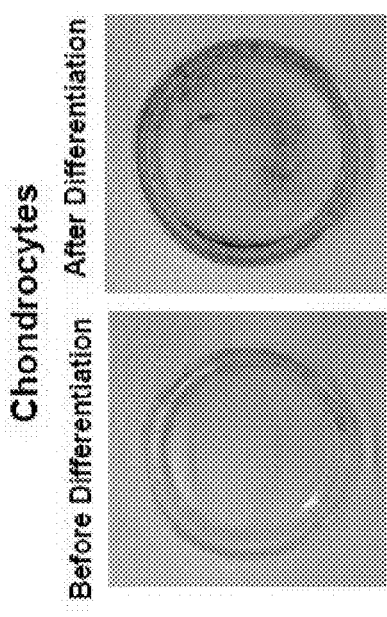
Chondrocytes
B. Induction of Osteogenic Differentiation
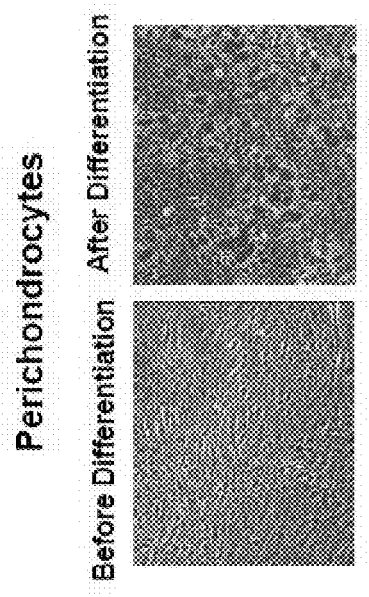
Perichondrocytes
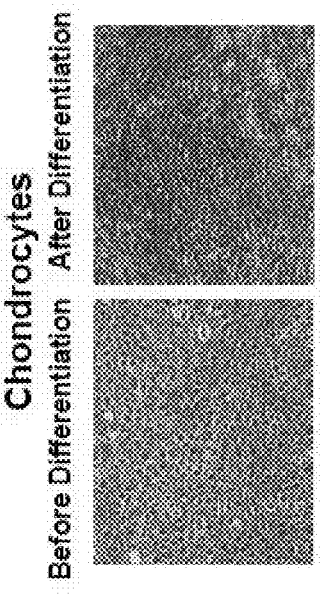
Chondrocytes Fig. 17
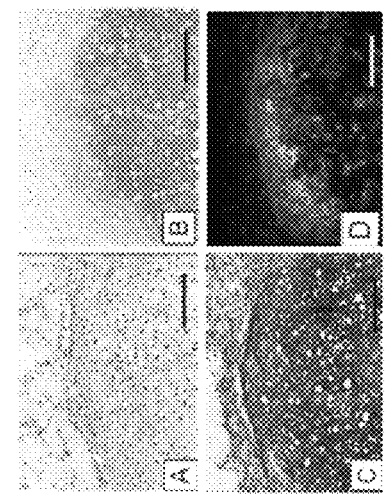
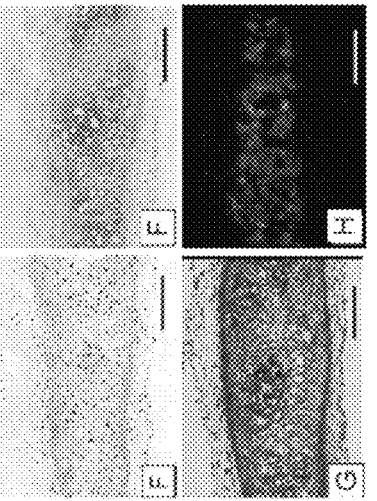
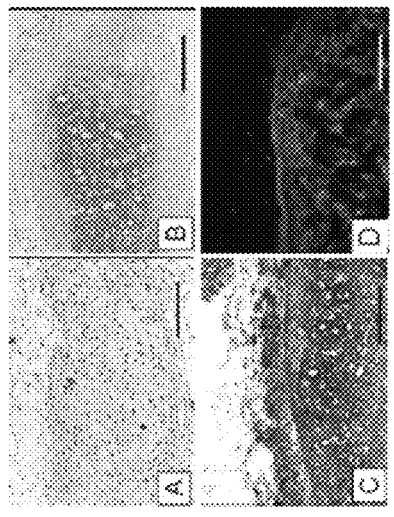
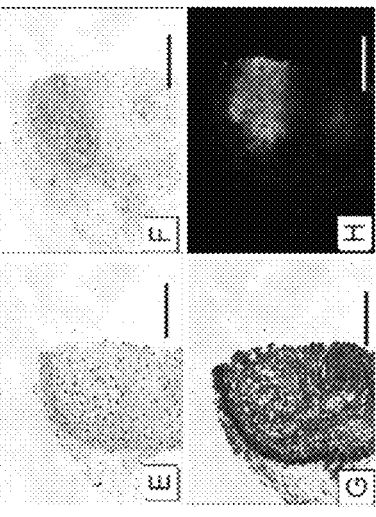

METHOD FOR PREPARATION OF CARTILAGE CELL

The present claims the benefit of an international application, PCT/JP2008/051327, filed on Jan. 23, 2008, which in turn claims priority to JP 2007-012160 filed on Jan. 23, 2007, all of which are incorporated herein by reference.

TECHNICAL FIELD

The present invention relates to a method of preparing chondrocytes. More specifically, the present invention relates to a method of preparing chondrocytes from perichondrocytes.

BACKGROUND ART

When human cartilage is congenitally deficient or becomes damaged or deficient in the course of lifetime, usually the cartilage is not regenerated. For treating diseases of such human cartilage, a method has been used in which a cartilage tissue is taken from a site of a patient and transplanted into the deficient site of the patient. However, this method has problems that the donor site and the amount of the tissue that can be taken are limited. Then, methods in which a part of autologous chondrocytes is taken, cultured ex vivo and returned to the deficient site have been developed (Non-Patent Documents Nos. 1-4) and applied clinically (Non-Patent Documents Nos. 5, 6 and 7).

However, these methods using chondrocytes have two problems: invasion into the donor site and retention of the shape of a regenerated tissue for a long time. The first one (invasion) is a problem that the donor site from which a cartilage tissue has been taken for culture may result in deformities, such as defect or recess, or dysfunction. The second one (retention of the shape for a long time) is a problem whether a tissue regenerated with cultured cartilage can retain its shape for a long time without being absorbed.

In order to solve these problems, other sources of chondrocytes have been sought for. That is, an idea has been contemplated in which cells other than chondrocytes are differentiated ex vivo into chondrocytes and returned into the living body. Examples of these cells include embryonic stem cells, mesenchymal stem cells, cells derived from the synovial membrane of knee joint, and adipocytes (Non-Patent Documents Nos. 1-4). All of these cells have been confirmed to differentiate into chondrocytes. However, clinical application of embryonic stem cells is difficult from an ethical viewpoint; collecting mesenchymal stem cells or cells derived from the synovial membrane of knee joint is difficult and highly invasive; differentiating adipocytes into chondrocytes is still under development; and mesenchymal stem cells have the problems of invasion and differentiation efficiency. Thus, any of these cells has not reached the stage of clinical application.

To date, in vivo and ex vivo researches have confirmed that perichondrium forms cartilage (Non-Patent Documents Nos. 8-10). In those researches, perichondrium is transplanted as a mass without being isolated. Such transplant is far from clinical application.

[Non-Patent Document 1]
van Osch G J et al, Plast Reconstr Surg 107:433-440 (2001)
[Non-Patent Document 2]
Brittberg et al, The New England Journal of Medicine 331:889-895 (1994)
[Non-Patent Document 3]
Ting et al, Annals of Plastic Surgery 40:413-421 (1998)
[Non-Patent Document 4]
Rodriguez et al, Plastic and Reconstructive Surgery 103: 1111-1119 (1999)
[Non-Patent Document 5]
Ochi M et al, J Bone Joint Surg 84:571-578 (2002)
[Non-Patent Document 6]
Yanaga H et al, Aesth Plast Surg 28: 212-221 (2004)
[Non-Patent Document 7]
Yanaga H et al, Plast & Reconstr Surg 117: 2019-30 (2006)
[Non-Patent Document 8]
Ove Engkvist et al., Scand J Plast Reconst Surg. 1979, 13; 275-280
[Non-Patent Document 9]
Ove Engkvist et al., Scand J Plast Reconst Surg. 1979, 13; 371-376
[Non-Patent Document 10]
Duynstee et al., Plasr and Reconst Surg. 2002, 110(4). 1073-1079
[Patent Document 1]
Japanese Unexamined Patent Publication No. 2005-511083
[Patent Document 2]
Japanese Unexamined Patent Publication No. 2003-51875
[Patent Document 3]
Japanese Unexamined Patent Publication No. 2005-500085
[Patent Document 4]
Japanese Unexamined Patent Publication No. 2001-103965

DISCLOSURE OF THE INVENTION

Problem for Solution by the Invention

It is an object of the present invention to provide a method of preparing chondrocytes which is less invasive to a donor site.

Means to Solve the Problem

Toward the solution of the above-described problems, the present inventors have developed a method of using perichondrium covering the outside of auricular cartilage or costicartilage. The present inventors have succeeded in producing proteoglycan and type II collagen (matrixes peculiar to chondrocytes) by isolating and proliferating perichondrocytes from perichondrium and differentiating the resultant perichondrocytes into chondrocytes in vivo or ex vivo.

The present invention may be summarized as follows.

(1) A cell derived from a human perichondrial tissue, the cell being capable of differentiating into a chondrocyte.
(2) The cell according to (1), wherein the human perichondrial tissue consists of its outermost layer and fibroblast layer.
(3) The cell according to (1), wherein the human perichondrial tissue consists of its outermost layer, fibroblast layer and innermost layer.
(4) A method of preparing the cell according to (1), wherein the method comprises culturing cells isolated from a human perichondrial tissue.
(5) A composition comprising the cell according to any one of (1) to (3).
(6) The composition according to (5) for use in proliferating a cell derived from a human perichondrial tissue, the cell being capable of differentiating into a chondrocyte.
(7) The composition according to (5) for use in preparing human chondrocytes.
(8) The composition according to (5) for use in cell transplant.

(9) The composition according to (8), wherein the cell transplant aims at any one of treatment of congenital auricular deformity, treatment of costicartilage defect, treatment of damage to articular cartilage, treatment of tracheal cartilage defect, rhinoplasty, genioplasty, plastic surgery of small facial recesses, corrective surgery of facial left-right asymmetry, corrective surgery around eyelids, or cosmetic surgery of face.

(10) The composition according to any one of (5) to (9), which further comprises a matrix produced by the cell according to (1).

(11) The composition according to any one of (5) to (10), which further comprises a scaffold.

(12) A method of preparing chondrocytes, comprising differentiating the cell according to (1) into chondrocytes.

(13) The method according to (12), wherein cell masses are formed by culturing the cell according to (1) in centrifuge tubes.

(14) The method according to (12), wherein the cell according to (1) is multi-layered by plate culture.

(15) The method according to any one of (12) to (14), wherein the cell according to (1) is proliferated and/or differentiated in a medium containing a serum.

(16) The method according to (15), wherein the serum is bovine serum.

(17) The method according to (15), wherein the serum is an autoserum.

(18) The method according to any one of (12) to (17), wherein the cell according to (1) is differentiated into chondrocytes in a medium containing DEME/F 12, a serum, antibiotics and antimycotics.

(19) The method according to (18), wherein the medium further contains dexamethasone and/or L-ascorbic acid.

(20) The method according to (18) or (19), wherein the medium further contains an insulin-like growth factor and/or a basic fibroblast growth factor.

(21) Chondrocyte prepared by the method according to any one of (12) to (20).

(22) A composition comprising the chondrocytes according to (21) and/or a cartilage tissue formed by the chondrocytes.

(23) The composition according to (22) for use in transplant treatment.

(24) The composition according to (23), wherein the transplant treatment aims at any one of treatment of congenital auricular deformity, treatment of costicartilage defect, treatment of damage to articular cartilage, treatment of tracheal cartilage defect, rhinoplasty, genioplasty, plastic surgery of small facial recesses, corrective surgery of facial left-right asymmetry, corrective surgery around eyelids, or cosmetic surgery of face.

(25) The composition according to any one of (22) to (24), which further comprises a matrix produced by the chondrocytes according to (21).

(26) The composition according to any one of (22) to (25), which further comprises a scaffold.

(27) A method of transplanting the cell according to any one of (1) to (3) into a living body.

(28) A method of transplanting the chondrocytes according to (21) and/or a cartilage tissue formed by the chondrocytes into a living body.

(29) Use of the cell according to any one of (1) to (3) for cell transplant.

(30) Use of the chondrocytes according to (21) and/or a cartilage tissue formed by the chondrocytes in transplant treatment.

(31) A method of preparing a matrix produced by chondrocytes, comprising differentiating the cell according to (1) into chondrocytes and allowing the chondrocytes to produce the matrix.

(32) The method according (31), wherein the matrix is type II collagen and/or proteoglycan.

EFFECT OF THE INVENTION

The method of preparing chondrocytes of according to the present invention need not collect a cartilage tissue. Therefore, it is possible to minimize the invasion into donor sites.

Further, by using perichondrocytes comprising cartilage stem/progenitor cells, the method of the present invention makes it possible to retain the shape of a regenerated tissue for a long time.

The present specification encompasses the contents described in the specification and/or the drawings of Japanese Patent Application No. 2007-012160 based on which the present patent application claims priority.

BRIEF DESCRIPTION OF THE DRAWINGS

The patent or application file contains at least one drawing executed in color. Copies of this patent or patent application publication with color drawings,(s) will be provided by the Office upon request and payment of the necessary fee.

While cartilage tissue is stained blue with Alcian blue, perichondrium is not stained. Only the outermost layer and the fibroblast layer of perichondrium may be collected. Alternatively, the outermost layer, the fibroblast layer and the innermost layer (zone of transition to the cartilage matrix) may be collected. a: before collection; arrow: perichondrium; b: perichondrium alone is being detached; c: perichondrium has been detached; d: the innermost layer of perichondrium (zone of transition to the cartilage matrix) may also be collected; e: collected perichondrium consisting of the outermost layer and the fibroblast layer alone. Alcian blue staining. Magnification: 200

FIG. 2. Centrifuge Tube Culture of Perichondrocytes

Like a cell mass of chondrocytes, a cell mass of perichondrocytes forms a cartilage tissue in a centrifuge tube. a: cartilage tissue regenerated from perichondrocytes; b: cartilage tissue regenerated from chondrocytes. Alcian blue staining. Bar: 200 μm FIG. 3. The matrix (proteoglycan)-producing capacity of perichondrocytes is enhanced by multi-layering in vitro, in the same manner as seen in chondrocytes. a: bright field; b: Alcian blue staining.

Figure 4:
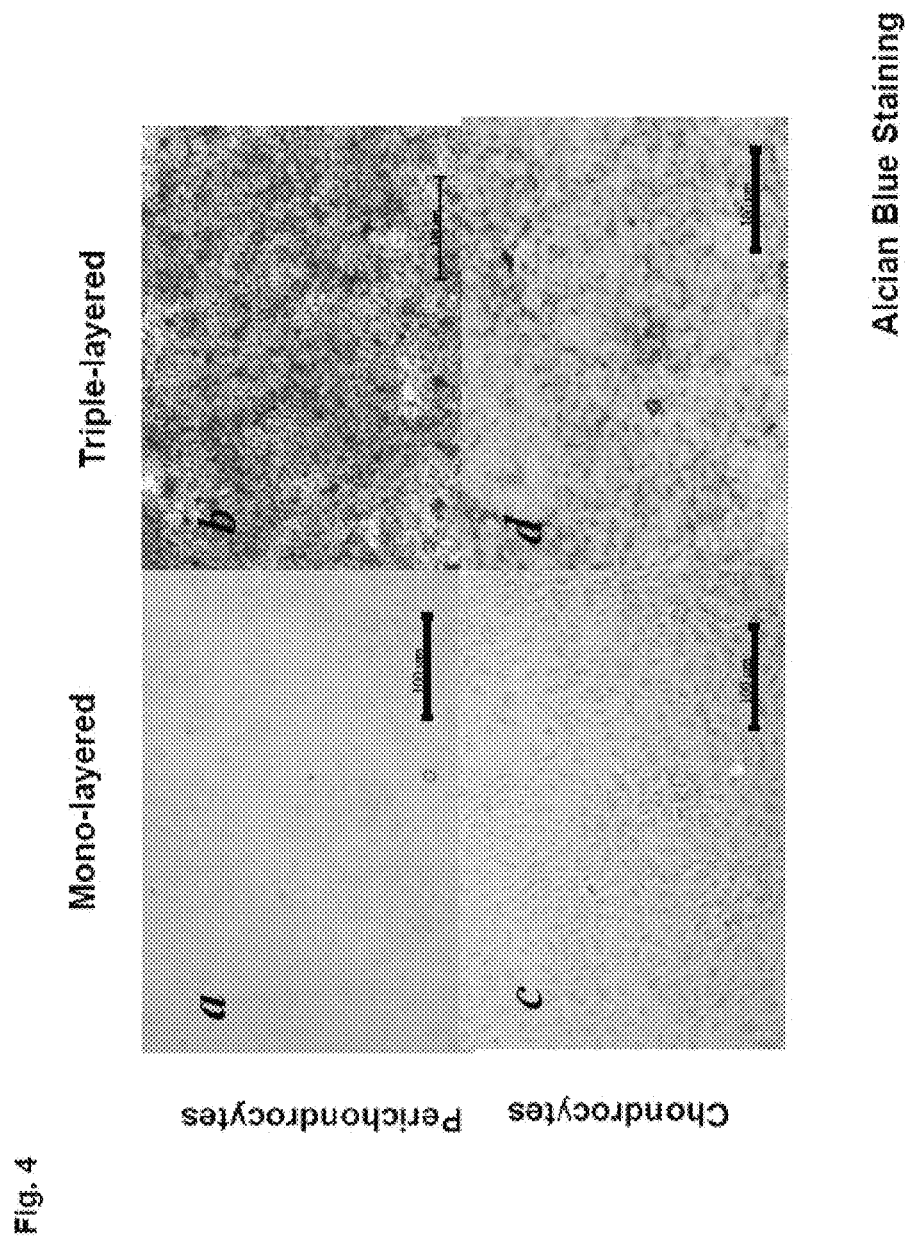

FIG. 4. The matrix (proteoglycan)-producing capacity of perichondrocytes is enhanced by multi-layering in vitro, in the same manner as seen in chondrocytes. The matrix-producing capacity of perichondrocytes is comparable to that of chondrocytes.

a: mono-layered perichondrocytes; b: multi-layered (triple-layered) perichondrocytes; c: mono-layered chondrocytes; d: multi-layered (triple-layered) chondrocytes. Alcian blue staining.

Figure 5:
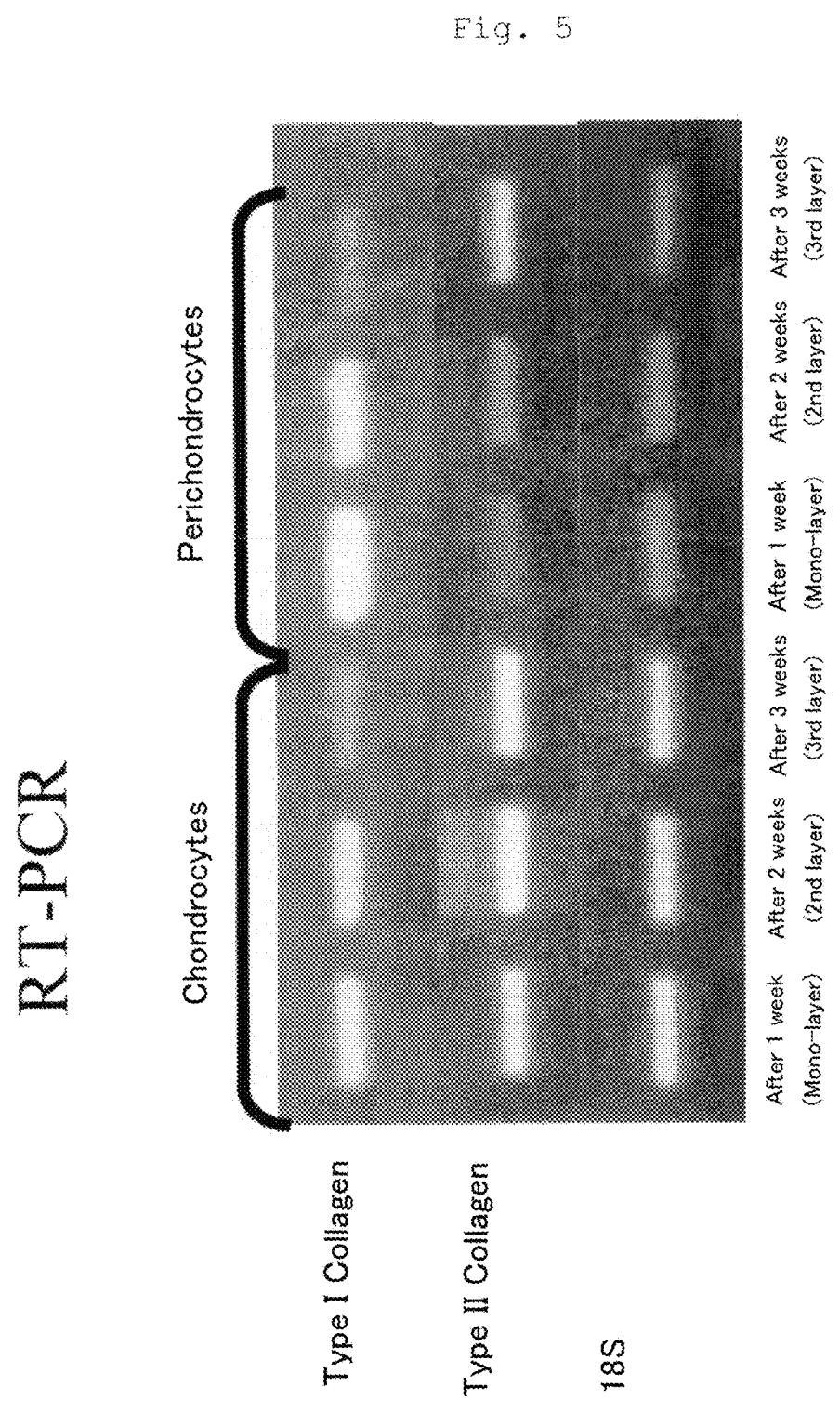

FIG. 5. RT-PCR in Multi-Layered Culture of Perichondrocytes and Chondrocytes

In perichondrocytes, type I collagen decreases and type II collagen increases as a result of multi-layering.

Figure 6:
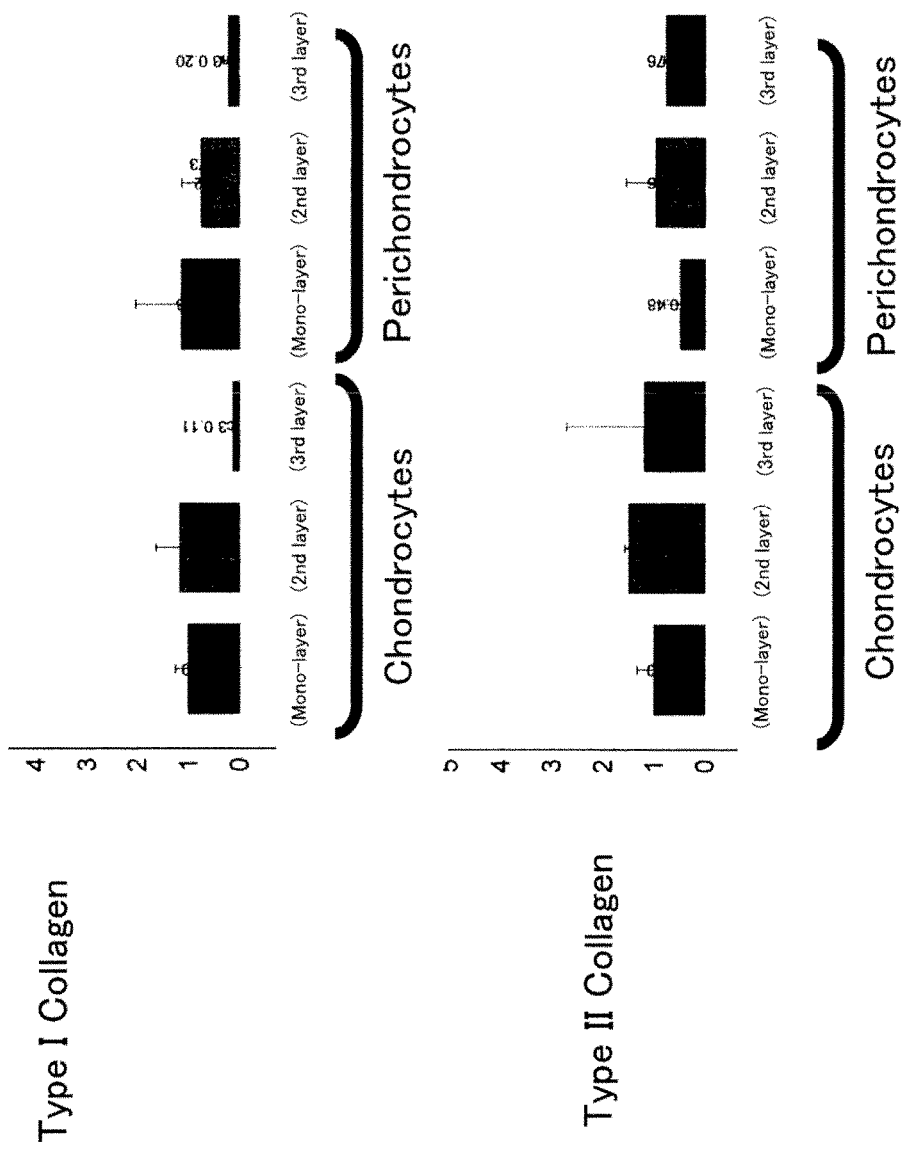

FIG. 6. Quantitative Determination by Real Time PCR in Multi-Layered Culture of Perichondrocytes and Chondrocytes In perichondrocytes, type I collagen tends to decrease and type II collagen tends to increase as a result of multi-layering.

Figure 7:
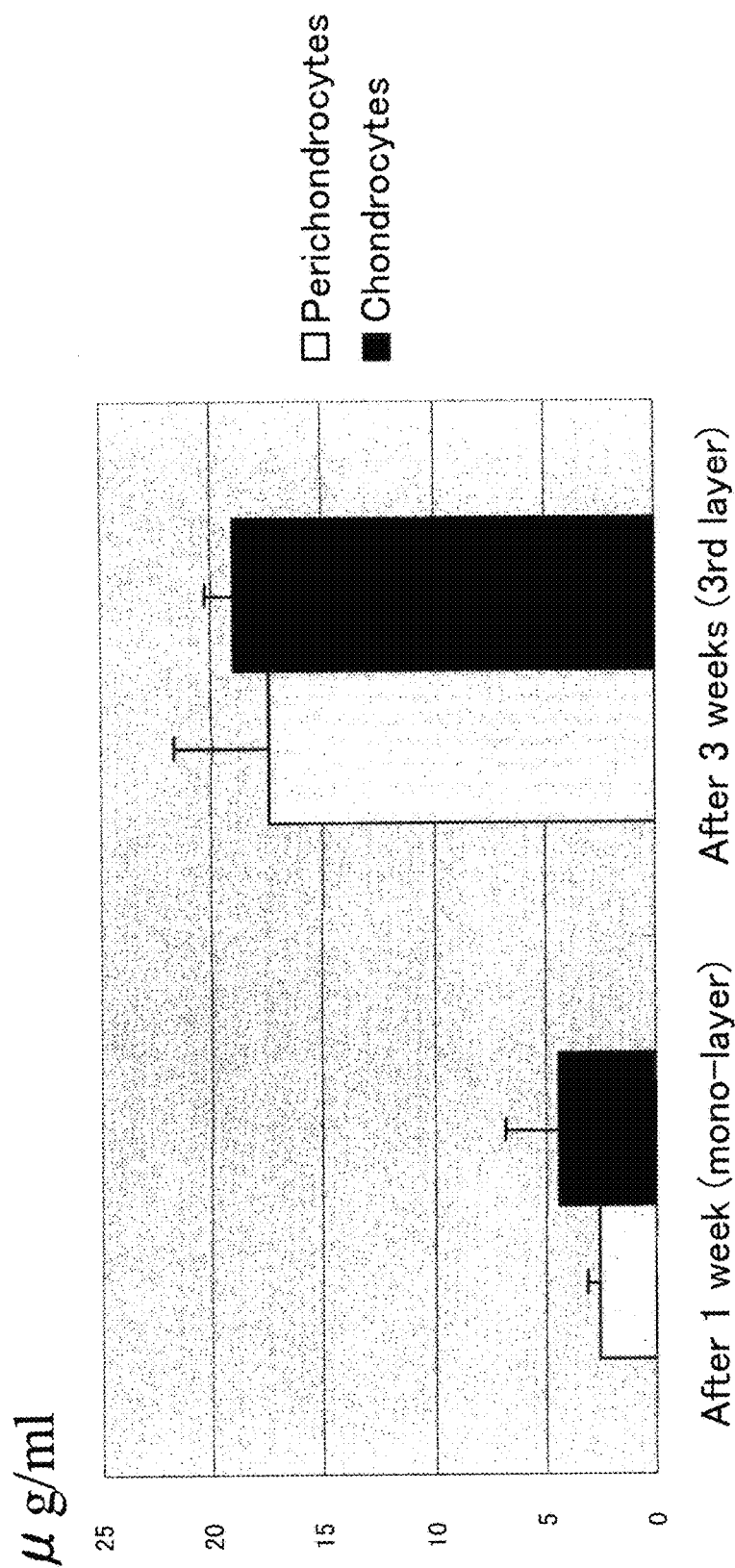

FIG. 7. Proteoglycan is produced in the supernatant as a result of multi-layering in vitro. The proteoglycan-producing capacity of perichondrocytes is almost comparable to that of chondrocytes.

Figure 8:
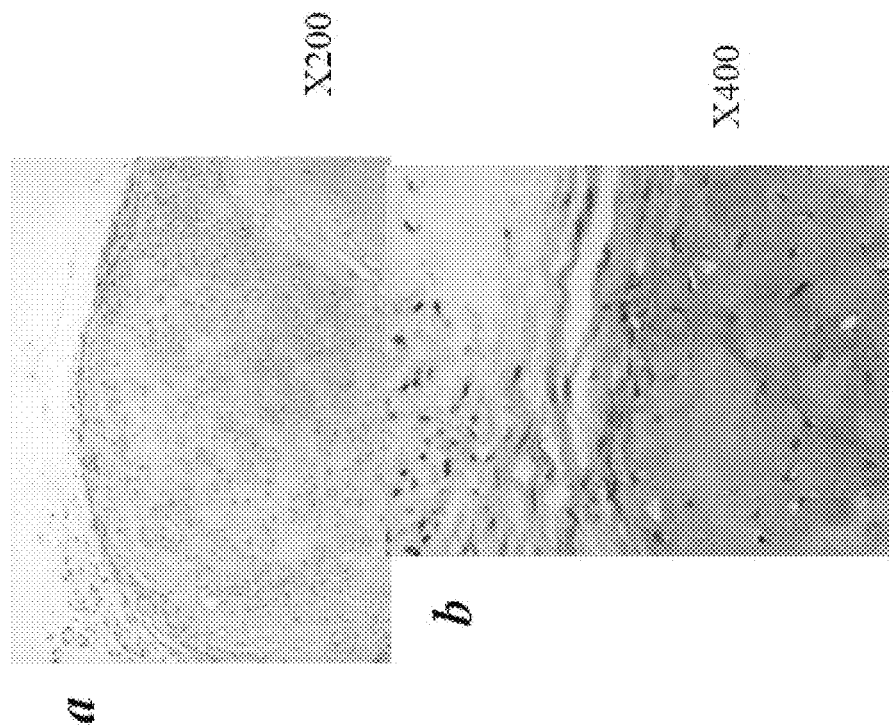

FIG. 8. Cultured human perichondrocytes form a cartilage tissue in, vivo.

This Figure shows the state after two months of subcutaneous transplanting of cultured perichondrocytes in the back of NOD/SCID mouse. Alcian blue staining. a: magnification 200; b: magnification 400

FIG. 9. Cultured human perichondrocytes produce type I and type II collagen and form a cartilage tissue in vivo.

This Figure shows the state after two months of subcutaneous transplanting of cultured perichondrocytes in the back of NOD/SCID mouse. Alcian blue staining. Type I collagen (red) and type II collagen (green). a: magnification 100; b: magnification 400

Figure 10:
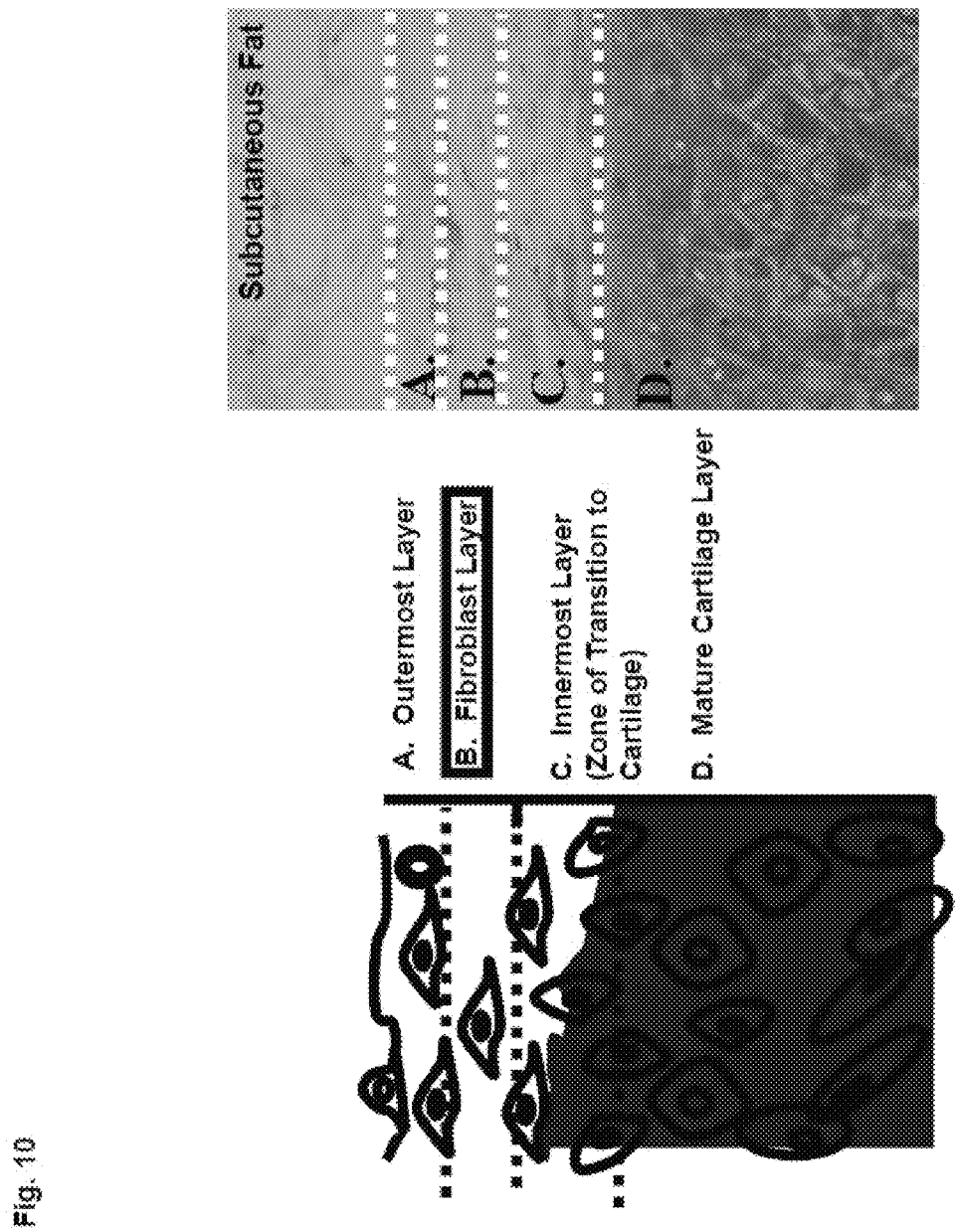

FIG. 10 shows the layer structure of perichondrium and cartilage such as elastic cartilage and hyaline cartilage.

Figure 1:
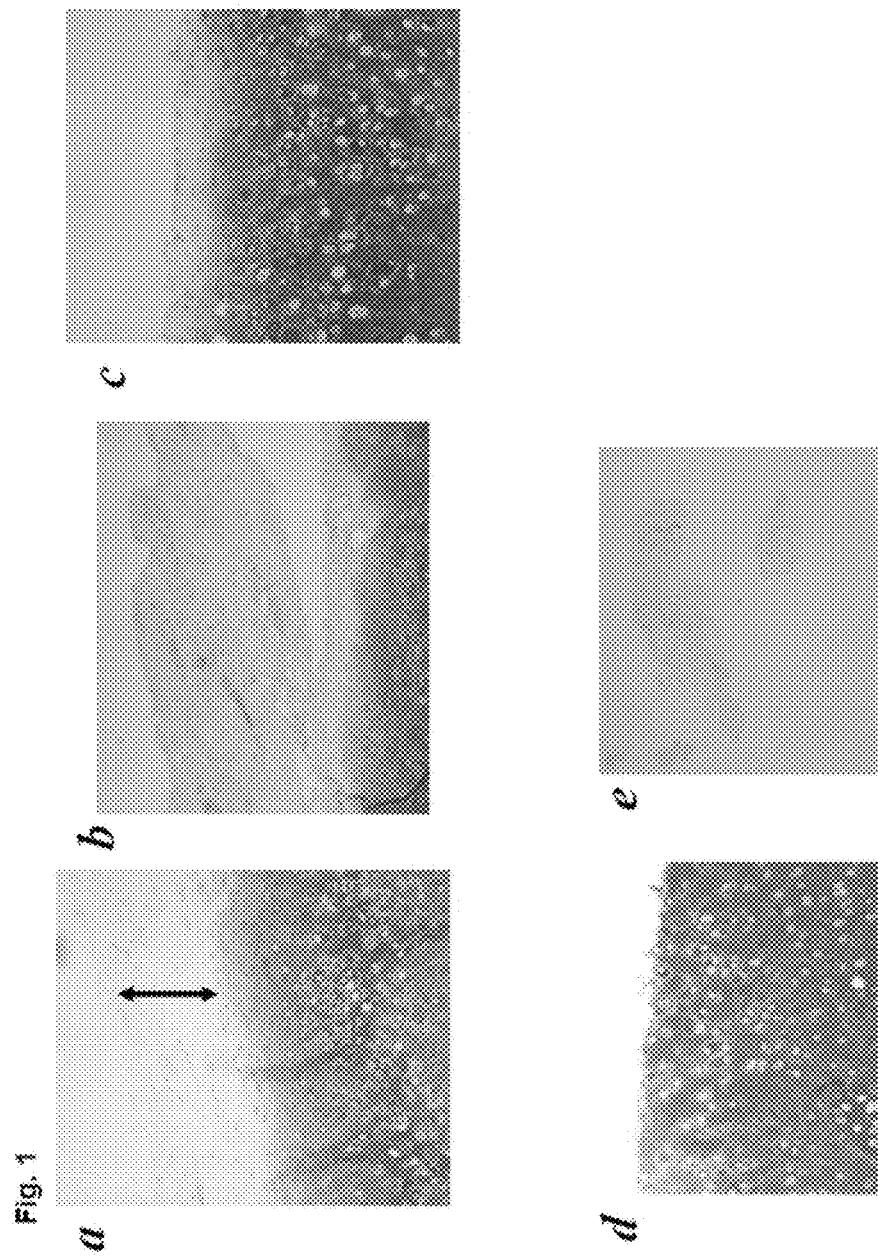
FIG. 1. Histological Examination of Human Perichondrium at the Time of Collection.
Figure 11:
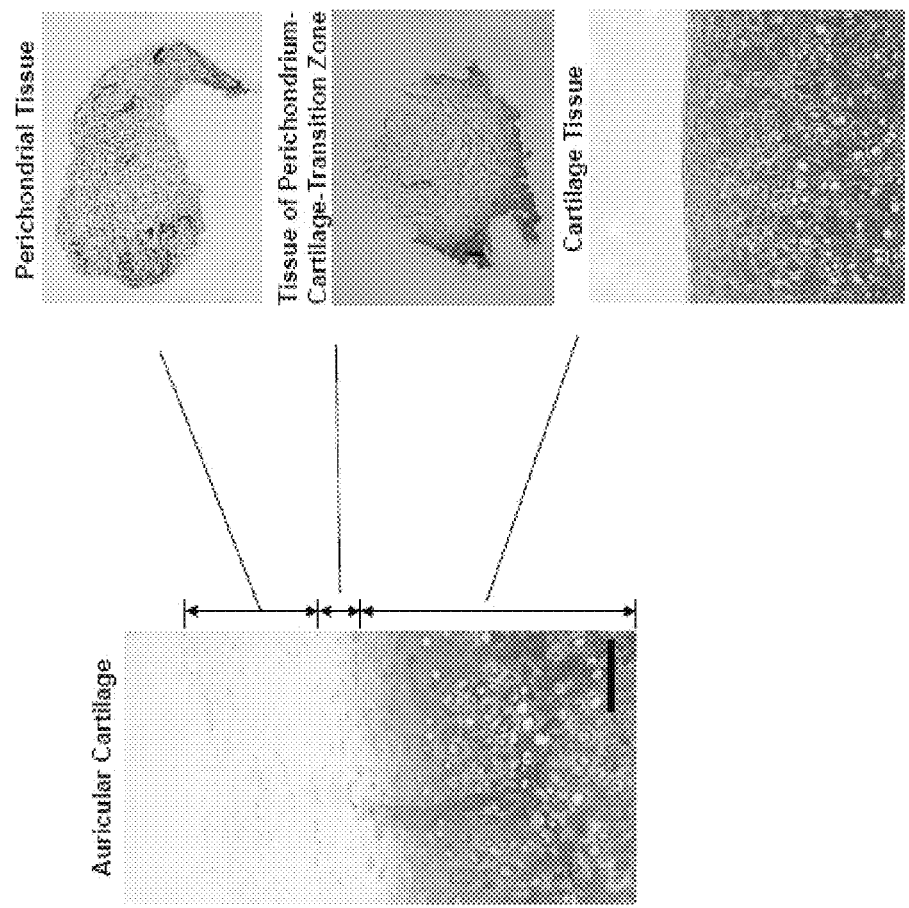

FIG. 11 supplements FIG. 1.

A human perichondrial tissue is collected in outermost layer and separate two layers of fibroblast layer and innermost layer. Those other than these layers fall under cartilage tissue. a: outermost layer and fibroblast layer; b: innermost layer; c: cartilage tissue. Alcian blue staining. Magnification: 200

Figure 12:
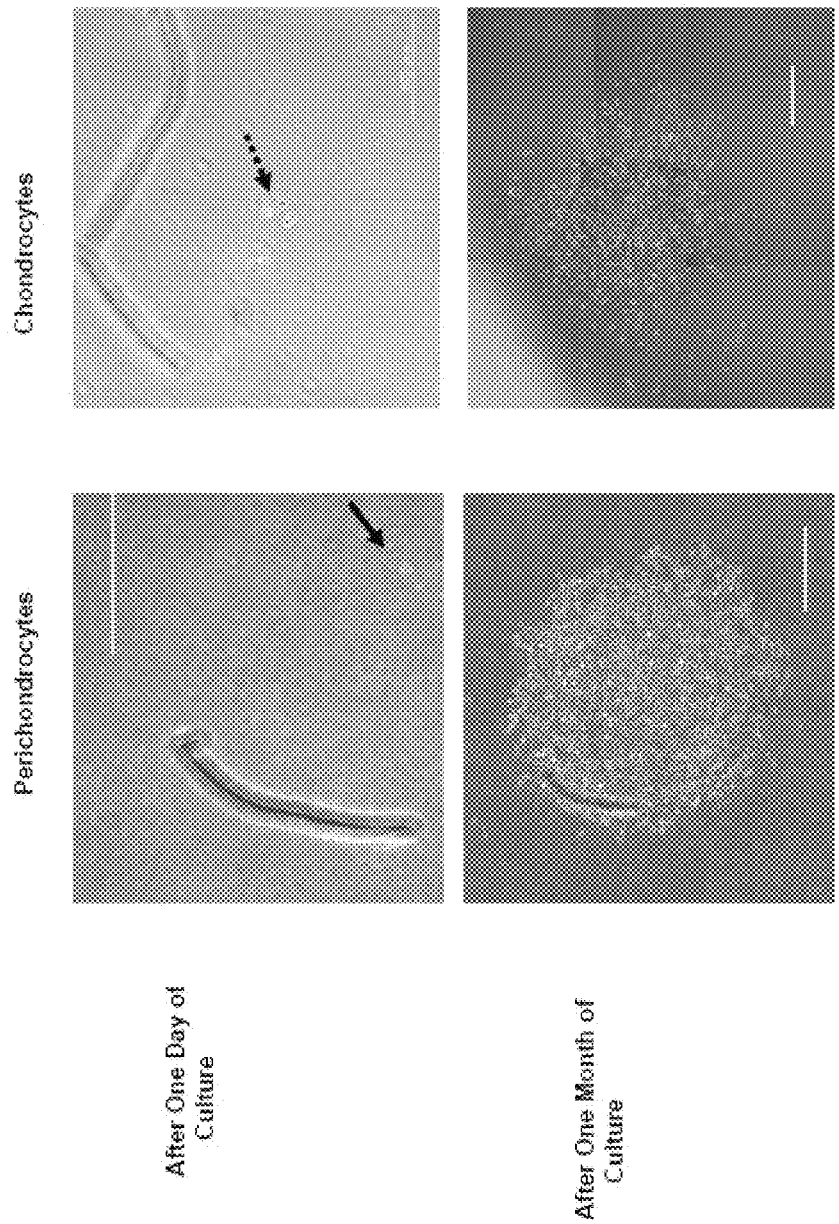

FIG. 12 The Growth Capacity of Human Perichondrocytes. This Figure shows microscopic comparison of the colony forming activities of perichondrocytes and chondrocytes. Compared to human chondrocytes, human perichondrocytes formed a larger colony after one month of culture. Human chondrocytes (dotted arrow). Human perichondrocytes (solid arrow). Scale bar: 500 µm FIG. 13 The Growth Capacity of Human Perichondrocytes. This Figure shows comparison of the colony-forming activities of human perichondrocytes, cells in the perichondrium-cartilage transition zone, and chondrocytes.

Perichondrocytes, cells in perichondrium-cartilage transition zone and chondrocytes were cultured for 14 days. Comparison of the numbers of colonies formed by 50 cells or more revealed that perichondrocytes have a high colony-forming activity. Thus, it was revealed that perichondrocytes have a high growth capacity localized therein.

(Briefly, 500 cells from each type of the above cells were plated in a 3.5 cm cell culture dish. Two weeks later, the number of colonies formed was counted. Those colonies formed by 50 cells or more were counted.)

*: $p<0.001$ (Mann Whitney U-Test with Bonferroni correction) n=27 (patient No.=3)

Figure 14:
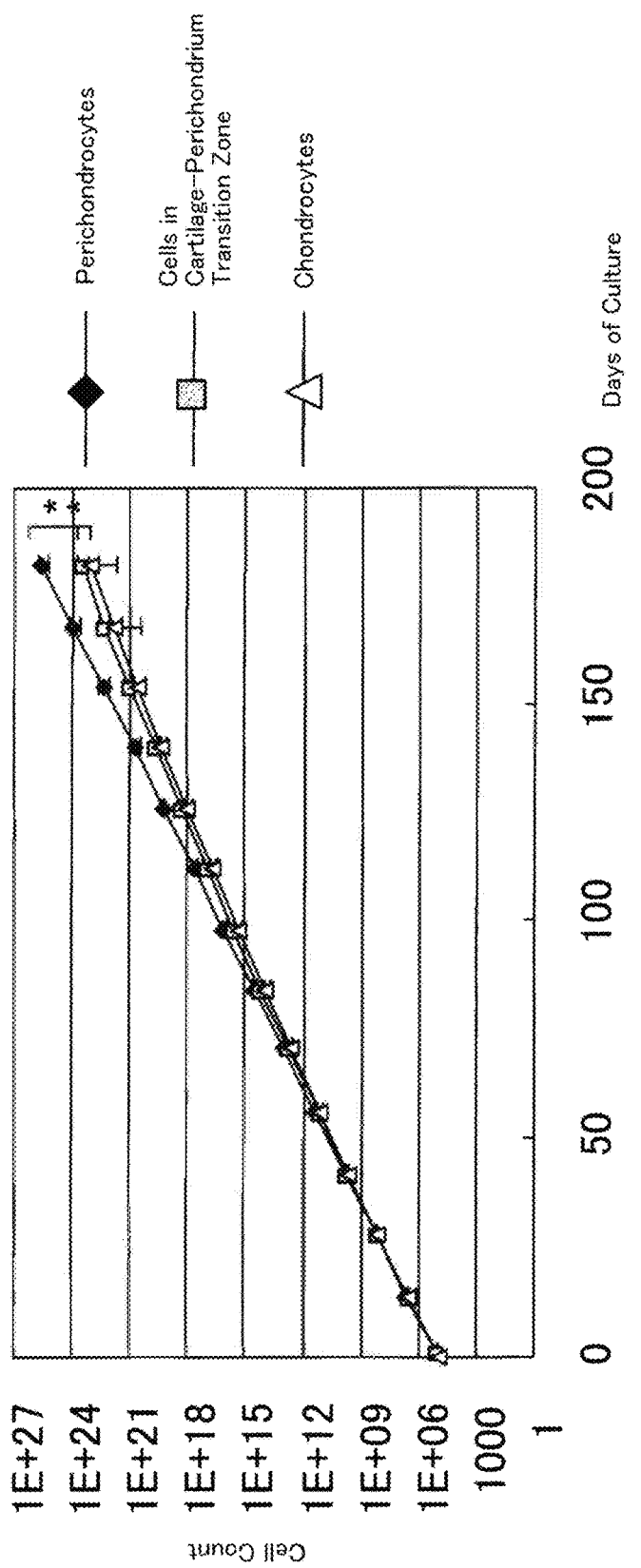

FIG. 14 The Growth Capacity of Human Perichondrocytes. This Figure shows comparison of the long-term growth capacities of human perichondrocytes, cells in the cartilage-perichondrium transition zone, and chondrocytes.

Perichondrocytes, cells in cartilage-perichondrium transition zone and chondrocytes were used to compare their growth capacities in long term culture. The results revealed that perichondrocytes have a high growth capacity.

*: $p<0.001$ (Mann Whitney U-Test with Bonferroni correction) n=5 (patient No.=5)

FIG. 15 In Vitro Induction of Differentiation into Lipid and Bone

Multipotency was examined in vitro. Panel A: Induction of lipid differentiation: while perichondrocytes formed lipid droplets and were stained with Oil red O (lipid staining reagent), chondrocytes did not form lipid droplets and were not stained with Oil red O. Panel B: Induction of bone differentiation: while perichondrocytes showed a large number of Ca deposits and were stained with alizarin red, chondrocytes showed no Ca deposits and were not stained with alizarin red. Thus, multipotency to lipid and bone was recognized in perichondrocytes.

Figure 16:
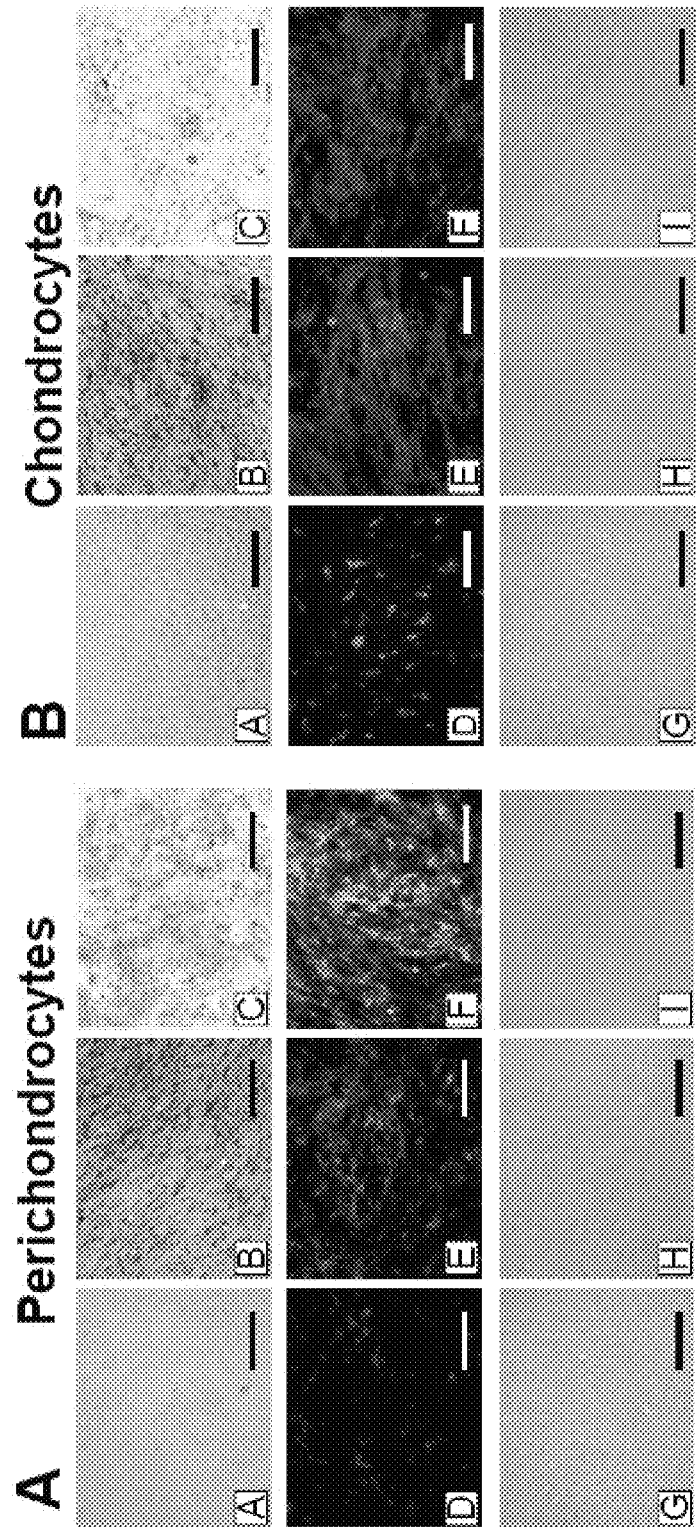

FIG. 16 In Vitro Induction of Differentiation into Cartilage

Panel A: Induction of Cartilage Differentiation in Human Perichondrocytes

The extracellular matrix-producing capacity was increased by (A) mono-layered, (B) double-layered and (C) triple-layered culture of perichondrocytes in a differentiation inducing medium. When perichondrocytes were stained with type I collagen (red), type II collagen (green) and DAPI (blue), it was also confirmed that the extracellular matrix-producing capacity was increased by (D) mono-layered, (E) double-layered and (F) triple-layered culture. When a differentiation inducing medium was not used, extracellular matrix was not produced even when (G) mono-layered, (H) double-layered and (I) triple-layered culture was performed.

A-C, G-I: Alcian blue staining; D-F: type I collagen staining (red), type II collagen staining (green) and DAP staining I (blue). Scale bar: 200 µm Panel B: Induction of Cartilage Differentiation in Human Chondrocytes The extracellular matrix-producing capacity was increased by (A) mono-layered, (B) double-layered and (C) triple-layered culture of chondrocytes in a differentiation inducing medium. When chondrocytes were stained with type I collagen (red), type II collagen (green) and DAPI (blue), it was also confirmed that the extracellular matrix-producing capacity was increased by (D) mono-layered, (E) double-layered and (F) triple-layered culture.

When a differentiation inducing medium was not used, extracellular matrix was not produced even when (G) mono-layered, (H) double-layered and (I) triple-layered culture was performed. Scale bar: 200 µm Thus, perichondrocytes differentiated into cartilage in vitro in almost the same manner as chondrocytes differentiated.

A-C, G-I: Alcian blue staining; D-F: type I collagen staining (red), type II collagen staining (green) and DAP staining I (blue). Scale bar: 200 µm FIG. 17 Histological Examination of Cartilage Tissues Regenerated in vivo from Human Perichondrocytes and Chondrocytes Panel A: Human Perichondrocytes-Derived and Human Chondrocytes-Derived Regenerated Cartilage Tissues after One Month of Transplant (A-D: perichondrocytes-derived cartilage tissue; E-H: chondrocytes-derived cartilage tissue)

While the human perichondrocytes-derived regenerated cartilage was covered with type I collagen, the chondrocytes-derived regenerated cartilage was not covered with type I collagen.

Panel B: Human Perichondrocytes-Derived and Human Chondrocytes-Derived Regenerated Cartilage Tissues after Three Months of Transplant (A-D: perichondrocytes-derived cartilage tissue; E-H: chondrocytes-derived cartilage tissue)

While the human perichondrocytes-derived tissue was covered with type I collagen in the same manner as seen one month after transplant, the chondrocytes-derived regenerated cartilage was not covered with type I collagen.

A, E: HE staining; B, F: Alcian blue staining; C, G: Elastica van Gieson staining; D, H: type I collagen staining (red), type II collagen staining (green) and DAP staining I (blue). Scale bar: 200 µm These results demonstrate that perichondrocytes regenerate cartilage in the same manner as chondrocytes do. Unlike from the chondrocytes-derived regenerated cartilage, the perichondrocytes-derived regenerated cartilage is covered with perichondrium. This suggests that perichondrocytes-derived regenerated cartilage is superior in long-term shape-retaining ability.

Figure 18:
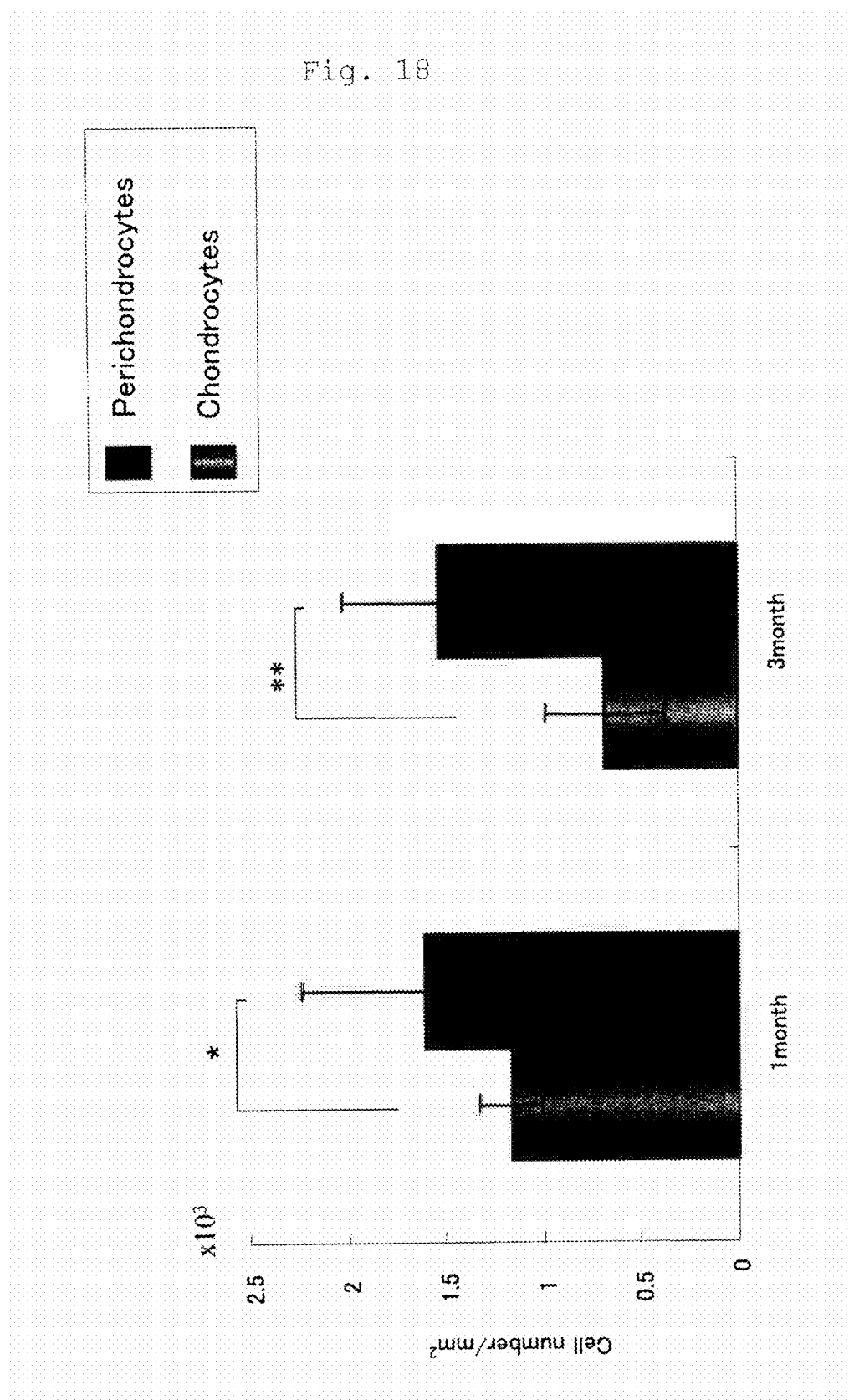

FIG. 18 Cell Count per mm$^2$ of in vivo Reconstructed Cartilage

This Figure shows the cell count per mm$^2$ of the cartilage portion in tissues removed one month and three months after transplant. While no change in cell count was observed in the perichondrocytes-derived tissue whether one month or three months passed after transplant, a decrease in cell count was observed in the chondrocytes-derived tissue three months after transplant.

*: p<0.05,**: p<0.01 (Mann Whitney U-Test)

These results indicate that perichondrocytes are superior to chondrocytes in long-term shape-retaining ability.

Figure 19:
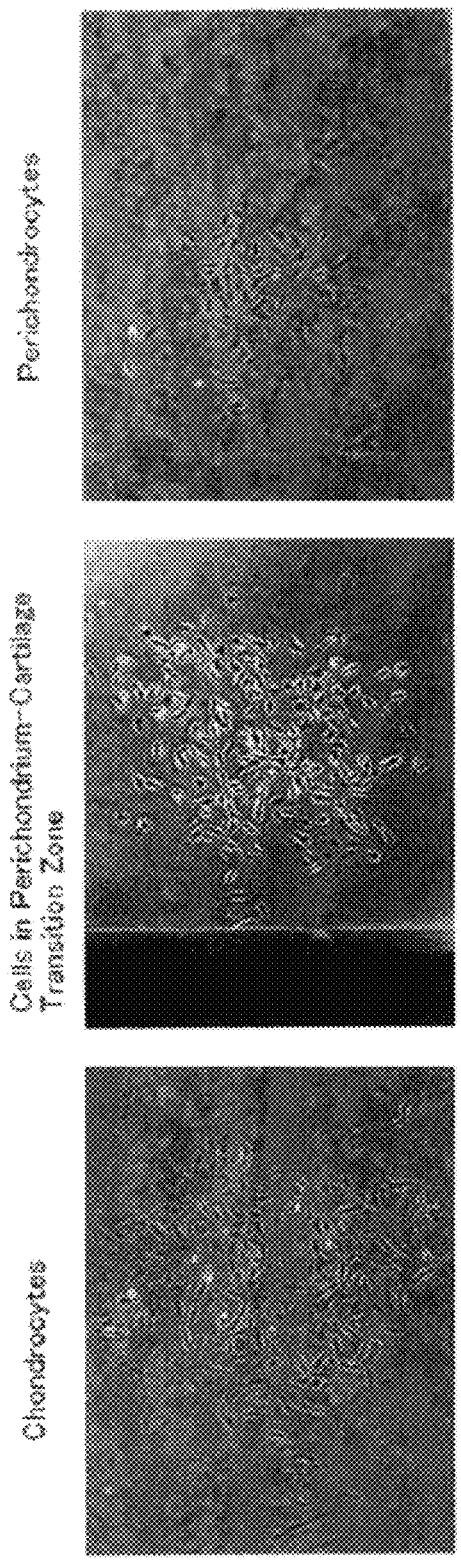

FIG. 19 Comparison of Colony Forming Activities in 10% Human Autoserum Medium between Human Perichondrocytes, Cells in Perichondrium-Cartilage Transition Zone, and Chondrocytes At day 9 of culture, human perichondrocytes formed a larger colony than human chondrocytes. Magnification: 40

Figure 20:
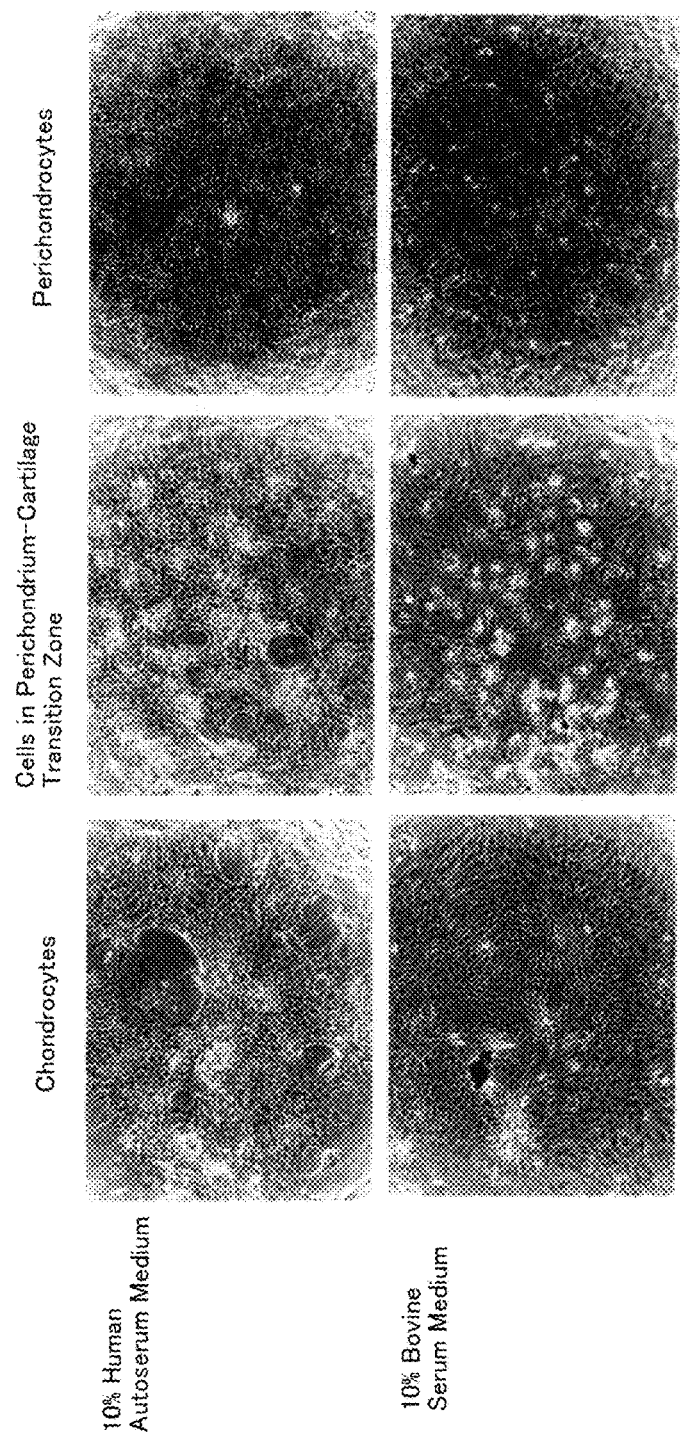

FIG. 20 Microscopic Comparison of Human Perichondrocytes, Cells in Perichondrium-Cartilage Transition Zone, and Chondrocytes after culture in 10% Human Autoserum Medium Each of the three types of cells cultured in 10% human autoserum medium reached confluency more quickly than in 10% bovine serum medium. Magnification: 40

BEST MODE FOR CARRYING OUT THE INVENTION

Hereinbelow, the present invention will be described in detail.

Conventionally, regeneration of human cartilage has been performed as follows: a cartilage tissue is collected as a mass, which is then treated with enzymes such as collagenase to isolate chondrocytes from the matrix components; the thus isolated chondrocytes are cultured for transplant treatment, especially autotransplantation.

In the present invention, however, not those chondrocytes present in the matrix but the very thin perichondrium surrounding such cells need be collected. Therefore, the collected perichondrium has substantially no chondrocytes present.

For example, perichondrium and cartilage such as elastic cartilage and hyaline cartilage are composed of four layers (FIG. 10). They are 1) outermost layer (including capillary vessels); 2) fibroblast layer (mainly consisting of perichondrocytes) (expressed as "perichondrocyte layer" in FIG. 10); 3) innermost layer (zone of transition to the cartilage matrix), and 4) mature cartilage layer (surrounded by the cartilage matrix) (see, for example, Bairati A, Comazzi M, Gioria M. et al., Tissue Cell 28: 455-68. (1996); Tonna et al., Labor. et al., Invest 31:609-632 (1974); Ellender et al., J. Anat 158:173-187 (1988)). The "outermost layer" is the uppermost of those layers expressing type I collagen but not expressing type II collagen, and includes capillary vessels. The "fibroblast layer" is a layer expressing type I collagen but not expressing type II collagen, and is entirely composed of perichondrocytes excluding the outermost layer. The "innermost layer" includes the "fibroblast layer" and the cartilage matrix that is expressing type II collagen and proteoglycan. The "mature cartilage layer" is a layer that is expressing type II collagen and proteoglycan but not expressing type I collagen.

In conventional cartilage collection methods, all the four layers 1) to 4), or two layers of 3) and 4), or layer 4) alone is collected. According to such conventional methods, the cartilage tissue at the donor site becomes deficient or can not be recovered. As a result, the donor site may present an ugly appearance such as recess or deformity.

In the present invention, a tissue section comprising 1) and 2) above or 1) to 3) above may be collected with sharp tools such as tweezers scissors. Alternatively, dull tools such as raspatories may be used. The layer 4) in which chondrocytes occupying the major part of cartilage tissue reside need not be collected. Therefore, it is possible to collect a tissue section with minimum invasion. It is a great advantage of the method of the present invention that no deficiency is caused in the cartilage tissue and thus no ugly appearance will occur. The thus obtained tissue section is isolated with collagenase or the like under specific conditions (e.g., 0.1-0.3% collagenase, 37° C., 1-3 hours). This is an isolation method peculiar to perichondrocytes. Alternatively, all the four layers 1) to 4) may be collected. When the resultant tissue section is isolated with collagenase or the like, perichondrocytes and chondrocytes may be separated from each other. For example, when the tissue section is treated with collagenase, perichondrocytes are isolated within three hours while chondrocytes need 10 to 16 hours for isolation. Using this time difference, it is possible to separate perichondrocytes and chondrocytes.

The thus isolated perichondrocytes are plated in culture dishes and cultured for about one week in a growth medium. Subsequently, the cells are centrifuge tube cultured, or mono-layer or multi-layer cultured in a differentiation inducing medium. By these procedures, it is possible to differentiate perichondrocytes into chondrocytes.

In the present invention, it is possible to differentiate perichondrocytes into chondrocytes by culturing those human perichondrocytes obtained from cartilage-free human perichondrium.

The present invention provides a cell derived from a perichondrial tissue, which is capable of differentiating into a chondrocyte. The cell of the present invention derived from a perichondrial tissue is believed to be a cartilage stem cell and/or a cartilage progenitor cell. The perichondrial tissue is part of the tissue composing cartilage tissue such as auricle or costicartilage, and includes perichondrium. Specifically, the perichondrial tissue is a tissue comprising the outermost layer and the fibroblast layer (perichondrocyte layer) or a tissue comprising the outermost layer, the fibroblast layer (perichondrocyte layer), and the innermost layer. The human perichondrial tissue from which the cell of the present invention is derived may consist of the outermost layer and the fibroblast layer. Alternatively, the human perichondrial tissue may consist of the outermost layer, the fibroblast layer, and the innermost layer. The perichondrial tissue may be a perichondrial tissue section collected from a human, especially a patient in need of cartilage transplant.

The cell derived from a perichondrial tissue may be a cell isolated from a perichondrial tissue or a cell obtained by subculturing the isolated cell.

In order to obtain the cell of the present invention, a perichondrial tissue section may be collected and cells may be isolated from the resultant tissue section. For collecting a perichondrial tissue section, sharp tools such as tweezers and scissors may be used. Alternatively, dull tools such as raspatories may be used. For isolation of cells from the perichondrial tissue section, the tissue section may be treated with collagenase under specific conditions (e.g., 0.1-0.3% collagenase, 37° C., 1-3 hours) and then centrifuged (e.g., 1500 rpm/5 min; twice). These treatment conditions may be appropriately changed, and such changed conditions are also within the scope of the present invention. By culturing the cells isolated from the perichondrial tissue section, it is possible to proliferate the cells and eventually to differentiate them into chondrocytes.

For primary culturing or subculturing the cell isolated from a perichondrial tissue section, the cell may be cultured in Dulbecco's Modified Eagles's Medium/Nutrient Mixture F12 (DMEM/F12) or Nutrient Mixture F-12 Ham (F-12 Ham), both supplemented with a serum (e.g., 10% fetal bovine serum (FBS) or a serum derived from the patient who is to receive transplant), at about 37° C. The medium may be exchanged every 2 to 4 days.

It is difficult to culture chondrocytes for a sufficiently long time to proliferate. On the other hand, it is possible to culture perichondrocytes for a relatively long time.

In order that the cells isolated from a perichondrial tissue section are differentiated into chondrocytes, the cells may be cultured in a medium containing a serum [for example, a medium containing DEME/F12, a serum (e.g., 10% FBS or a serum derived from the patient who is to receive transplant), antibiotics and antimycotics] at about 37° C. As a drug containing both antibiotics and antimycotics, antibiotic antimycotic solution SIGMA A5955 or the like may be used. To the medium, 40-60 µg/ml dexamethasone and/or 30-60 µg/ml L-ascorbic acid may be added further. Still further, an insulin-like growth factor (e.g., 5-10 ng/ml insulin-like growth factor-1 (IGF-1) or 5-10 ng/ml basic fibroblast growth factor (bFGF)) may also be added. Still further, 5-10 ng/ml insulin or the like may be added. The medium may be exchanged every 2 to 3 days.

It is possible to allow formation of a cell mass by culturing the perichondrial tissue-derived cell in a centrifuge tube. For example, a cell mass is formed when the cell is cultured in a centrifuge tube in serum-free DMEM/F12 medium containing 5 ng/ml insulin-like growth factor-1 (IGF-1), 5 ng/ml basic fibroblast growth factor (bFGF), 40 ng/ml dexamethasone and L-ascorbic acid, 1% antibiotic antimycotic solution, and insulin/transferrin/serine (ITS) at about 37° C. for 2 to 4 weeks.

The perichondrial tissue-derived cell may be mono-layered or multi-layered by plate culture. For example, when the cell is plate cultured in DMEM/F12 medium containing 10% FBS and 1% antibiotic antimicotic solution or DMEM/F12 medium containing 10% FBS, 1% antibiotic antimicotic solution, 5 ng/ml IGF-1, 5 ng/ml bFGF and 40 ng/ml dexamethasone and layered every one week, the matrix (e.g., proteoglycan) producing capacity of the cell is enhanced. Although the number of times of layering varies depending on the purpose or the size of tissue needed, usually 3 to 5 times is appropriate.

The above-described composition of the medium and the contents of individual components may be changed appropriately, and such changed composition and contents are also within the scope of the present invention.

Therefore, the present invention provides a method of preparing a cell capable of differentiating into a chondrocyte, comprising culturing cells isolated from a perichondrial tissue.

Further, the present invention provides a method of preparing chondrocytes, comprising differentiating a cell derived from a perichondrial tissue into a chondrocyte. Generally, perichondrocytes and chondrocytes produce different substances. It is known that perichondrocytes are present in type I collagen whereas chondrocytes are present in type II collagen and proteoglycan, and that they produce these substances. It is possible to discriminate perichondrocytes from chondrocytes by these products they produce.

Further, the present invention also provides chondrocytes prepared by differentiating a cell derived from a perichondrial tissue into a chondrocyte.

By transplanting a perichondrial tissue-derived cell capable of differentiating into a chondrocyte to a living body, it is possible to perform treatment of congenital auricular deformity, treatment of costicartilage defect, treatment of damage to articular cartilage (e.g., knee osteoarthritis), treatment of tracheal cartilage defect, rhinoplasty, genioplasty, plastic surgery of small facial recesses, corrective surgery of facial left-right asymmetry corrective surgery around eyelids, cosmetic surgery of face, and so on. For cell transplant, matrixes produced by these cells (e.g., type I and type II collagen, proteoglycans such as aggrecan) may also be added. Further, perichondrial tissue-derived chondrocytes may also be added. The perichondrial tissue may be a section collected from a human, especially a patient in need of cartilage transplant. For obtaining chondrocytes, a perichondrial tissue may be collected and then cells may be isolated from the collected tissue. For isolation of cells from the perichondrial tissue, the latter may be treated with collagenase under specific conditions (e.g., 0.1-0.2% collagenase, 37° C., 10-16 hours). If chondrocytes are added to a different culture system or to chondrocytes for the purpose of increasing the cell count in primary culture, the cell count necessary for transplant can be prepared in a shorter period of time because the cell count in the primary culture is large from the beginning. For cell transplant, prepared cells may be transplanted without any additives. Alternatively, substances such as type I and type II collagen or proteoglycan may be added.

Cell transplant may be performed by a method in which a perichondrial tissue-derived cell capable of differentiating into a chondrocyte is injected into an affected area with a syringe.

If a perichondrial tissue-derived cell capable of differentiating into a chondrocyte is co-cultured with a scaffold (cartilage treating material), a cartilage tissue possessing a three-dimensional structure can be formed. Examples of scaffold materials include collagen, polylactic acid, polyglycolic acid, copolymer of polylactic acid and polyglycolic acid, and non-absorbable materials such as polyethylene.

Further, chondrocytes prepared by differentiating a perichondrial tissue-derived cell into a chondrocyte and/or a cartilage tissue formed by these chondrocytes may be used to perform transplant treatment aiming at treatment of congenital auricular deformity, treatment of costicartilage defect, treatment of damage to articular cartilage (e.g., knee osteoarthritis), treatment of tracheal cartilage defect, rhinoplasty, genioplasty, plastic surgery of small facial recesses, corrective surgery of facial left-right asymmetry, corrective surgery around eyelids, cosmetic surgery of face, and so on. For transplant treatment, matrixes produced by these chondrocytes (e.g., type I and type II collagen, proteoglycan or aggrecan) may also be added. Further, chondrocytes derived from a cartilage tissue may also be added. The method of obtaining chondrocytes and the advantage of chondrocyte addition are as described above. Further, by placing an absorbable or non-absorbable material at the bottom of a culture vessel during cell culture, it is possible to allow the perichondrocytes to enter the material. The resultant material may directly be transplanted into an affected area.

Transplant of chondrocytes may be performed by injecting the cells into an affected area with a syringe.

Transplant of a cartilage tissue using a scaffold may be performed by a surgical transplant operation. For example, surgical techniques such as surgery practiced in rhinoplasty or otoplasty may be used.

Further, the present invention provides a method of preparing a matrix produced by chondrocytes, comprising differentiating perichondrocytes into chondrocytes and allowing the chondrocytes to produce the matrix. Examples of matrixes produced by chondrocytes include type II collagen and proteoglycan. These matrixes may be used in cosmetics, foods, health foods, pharmaceuticals, and so on.

Hereinbelow, the present invention will be described more specifically with reference to the following Examples. However, the scope of the present invention is not limited by those Examples.

EXAMPLE 1

Hereinbelow, the term "perichondrial tissue" at the time of collection refers histologically to the outermost layer and the fibroblast layer; and the term "tissue of perichondrium-cartilage transition zone" refers to the innermost layer.

Collection of Perichondrocytes

In order to collect a perichondrial tissue from a cartilage tissue such as auricular cartilage or costilcartilage (perichondria obtained from human auricular cartilage and left over after surgical operation were used with an approval obtained from patients or their parents; approval was also obtained from Kanagawa Prefectural Children Medical Center and the Ethics Committee of Yokohama City University Hospital), sharp tools such as tweezers and scissors were used. Alternatively, dull tools such as raspatories may be used. When sharp tools were used, a tissue section was prepared for each individual and examined for confirmation that the perichondrium alone had been collected (FIG. 1).

From the resultant tissue section, every tissue on the perichondrium (such as adipose tissue) was removed. Subsequently, the perichondrium was collected manually with sharp tools such as scissors.

The thus obtained perichondrial tissue was stained with Alcian blue (staining peculiar to cartilage matrix), and the staining was examined for each individual. While the perichondrial tissue was not at all stained with Alcian blue, a part of the tissue in perichondrium-cartilage transition zone and the entire part of cartilage tissue were stained (FIG. 11).

Isolation of Perichondrocytes

The thus obtained perichondrium was cut into pieces with scissors or surgical knives and shaken in 0.1-0.3% collagenase at 37° C. for 1-3 hours. Subsequently, the perichondrium was centrifuged (1500 rpm/5 min; twice) and the resultant precipitate was recovered. By these procedures, perichondrocytes could be isolated.

Primary Culture of Perichondrocytes

The perichondrocytes obtained as described above were plate cultured in Dulbecco's Modified Eagles's Medium/Nutrient Mixture F12 (DMEM/F12) supplemented with 10% fetal bovine serum (FBS) at 37° C. while exchanging the medium twice a week. The cells were grown densely within 2 weeks. These cells were used in subculture. The cells were grown densely in 7 to 10 days. It was possible to continue subculture for at least 6 months.

Differentiation of Perichondrocytes into Cartilage a) Perichondrocytes were precipitated by centrifugation (1500 rpm/5 min; twice) to form a cell mass. This cell mass was cultured in serum-free DMEM % F12 medium containing 5 ng/ml insulin-like growth factor-1 (IGF-1), 5 ng/ml basic fibroblast growth factor (bFGF), 40 ng/ml dexamethasone, 30-60 µg/ml L-ascorbic acid, 1% antibiotic antimycotic solution, and 1% insulin/transferrin/serine (ITS) for 3 to 4 weeks. The resultant white material was stained with Alcian blue. As a result, extracellular matrixes were stained blue, suggesting the presence of aggrecan (a cartilage marker). This result was almost comparable to the result on a cell mass formed by chondrocytes obtained by a similar technique (FIG. 2).

Chondrocytes were collected with dull tools such as raspatories. Subsequently, the cells were precipitated by centrifugation (1500 rpm/5 min; twice) to form a cell mass. This cell mass was cultured in serum-free DMEM/F12 medium containing 5 ng/ml insulin-like growth factor-1 (IGF-1), 5 ng/ml basic fibroblast growth factor (bFGF), 40 ng/ml dexamethasone, 30-60 µg/ml L-ascorbic acid, 1% antibiotic antimycotic solution, and 1% insulin/transferrin/serine (ITS) for 3 to 4 weeks.

b) Over plate-cultured perichondrocytes in a dense state, perichondrocytes were further seeded. As a medium, DMEM/F12 containing 10% FB and 1% antibiotic antimycotic solution, or DMEM/F12 containing 10% FBS, 1% antibiotic antimycotic solution, 5 ng/ml IGF-1, 5 ng/ml bFGF and 40 ng/ml dexamethasone was used.

Figure 3:
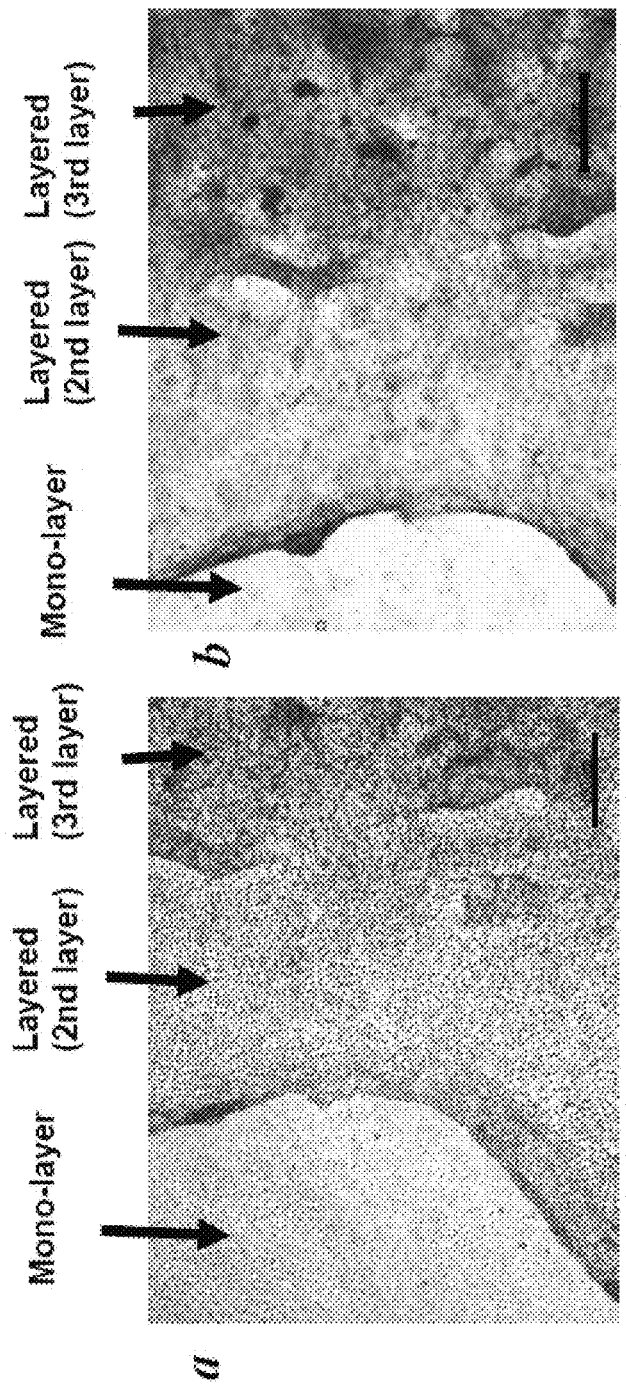

Cells were cultured using the latter medium. Perichondrocytes and chondrocytes at week 1 and week 3 of culture were stained with Alcian blue (FIGS. 3 and 4). Reverse transcription-polymerase chain reaction (RT-PCR) (FIG. 5) and quantitative PCR (FIG. 6) were performed, followed by comparison of the results. Alcian blue staining was performed after formalin fixation in a similar manner as used on the tissue section. As a result of Alcian staining, cells were stained blue on cell culture dishes. For use in RT-PCR and quantitative PCR, RNA was extracted from perichondrocytes and chondrocytes. RNA extraction was performed with RAeasy (QIAGEN) according to kit's the protocol. From the resultant RNA, cDNA was obtained using RNA PCR kit (Takara). As RT-PCR primers, F: atgctcagctttgtggatacgcgg (SEQ ID NO: 1) and R: aggaaagccacgagcaccct-gtgg (SEQ ID NO: 2) were used for type I collagen; F: catcattgacattgcacccatg (SEQ ID NO: 3) and R: ttagtttcct-gtctctgcccttg (SEQ ID NO: 4) were used for type II collagen; and F: caggtgaagactttgtggacatcc (SEQ ID NO: 5) and R: cctcctcaaaggtcagcgagtagc (SEQ ID NO: 6) were used for aggrecan. As quantitative PCR primers, type I collagen: Hs00266273_m1, type II collagen: Hs00164099_m1 and aggrecan: Hs00202971_m1 of Taqman Gene Expression Assays (Applied Biosystems) were used.

The results revealed that type I collagen (perichondrium marker) decreased and type II collagen (cartilage marker) increased. Thus, it was suggested that perichondrocytes differentiated into chondrocytes. Further, proteoglycan produced by chondrocytes was quantitatively determined by collecting the supernatant in the cell culture dish and subjecting it to enzyme linked immunosorbent assay (ELISA) using Blyscan (Biocolor). As a result, perichondrocytes exhibited a proteoglycan producing capacity comparable to that of chondrocytes (FIG. 7).

From these results, no big difference was recognized between perichondrocytes and chondrocytes with respect to differentiation into chondrocytes. It was suggested that perichondrocytes possess a cartilage differentiation capacity almost comparable to that of chondrocytes.

Transplant of Perichondrocytes

The cells from the above-described culture b) were harvested with a cell lifter and transplanted subcutaneously at the back of severe immunodeficiency mice (Sankyo, Japan). The cells were collected two months after the transplant and examined histologically. In order to examine the collected tissue histologically, the tissue was thinly sliced to prepare tissue samples. The tissue samples were subjected to Alcian blue staining to stain proteoglycan, a matrix peculiar to cartilage tissue. Further, immunostaining was performed for type II collagen that is a matrix of cartilage tissue and for type I collagen that is a cover around the cartilage. As a result, the extracellular matrix of cartilage tissue was stained blue in Alcian blue staining; this suggested the presence of proteoglycan, a cartilage marker (FIG. 8). Further, the extracellular matrix of cartilage tissue was stained with type II collagen, and the tissue around the cartilage was stained with type I collagen (FIG. 9). Thus, it was confirmed that cultured perichondrocytes form a cartilage tissue when transplanted.

Comparison of Perichondrocyte and Chondrocyte Colonies In Vitro

Colony assay was performed on the resultant perichondrocytes and chondrocytes. Each type of cells was seeded in 35 mm easy grip cell culture dishes to give a density of 1 cell/cm$^2$. Cells were cultured using Dulbecco's modified Eagle's medium and Ham's F-12 medium containing 10% fetal bovine serum and 1% antibiotic antimycotic solution in an incubator set at 37° C. under 5% $CO_2$. Starting 24 hours after the seeding, the medium was exchanged once in every 3 days. After one-month culture, formed colonies were observed under a microscope and photographed. As a result, perichondrocyte colonies were larger than chondrocyte colonies (FIG. 12).

Figure 13:
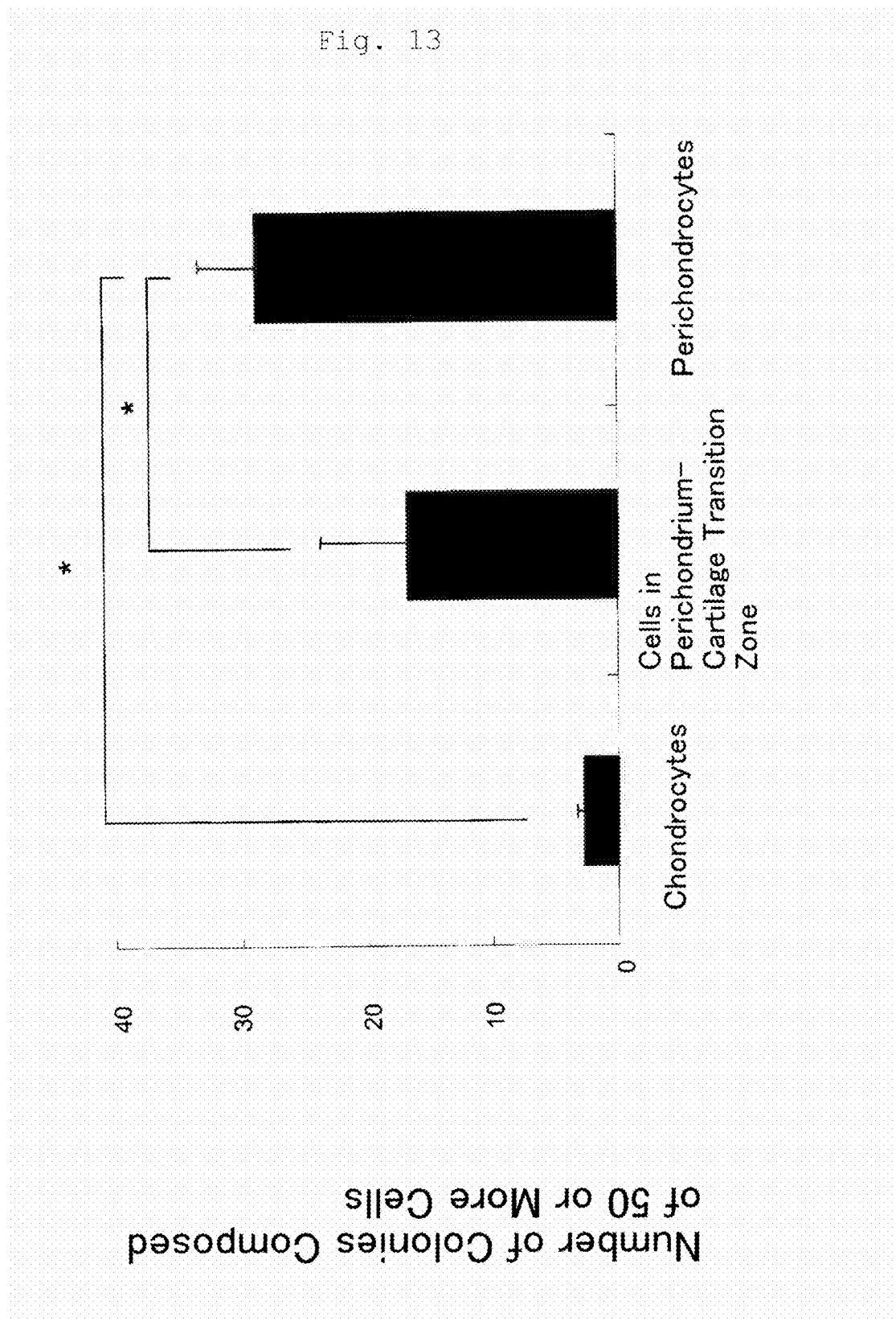

Comparison of Colony Forming Activities between Human Perichondrocytes, Cells in Perichondrium-Cartilage Transition Zone, and Chondrocytes Colony assay was performed on the resultant perichondrocytes, cells in perichondrium-cartilage transition zone, and chondrocytes. Each type of cells was seeded in 35 mm easy grip cell culture dishes to give a density of 52 cells/cm$^2$. Cells were cultured using Dulbecco's modified Eagle's medium and Ham's F-12 medium containing 10% fetal bovine serum and 1% antibiotic antimycotic solution in an incubator set at 37° C. under 5% $CO_2$. Starting 24 hours after the seeding, the medium was exchanged once in every 3 days. Colony numbers were counted after 14-day culture. A cell population consisting of 50 or more cells was counted as one colony. Comparison of colony numbers revealed the following order of colony forming activities: perichondrocytes>cells in perichondrium-cartilage transition zone>chondrocytes (FIG. 13).

*: $p<0.001$ (Mann Whitney U-Test with Bonferroni correction) n=27 (patient No.=3)

Comparison of the Long-Term Growth Capacities of Human Perichondrocytes, Cells in the Cartilage-Perichondrium Transition Zone, and Chondrocytes Long-term growth capacity was examined on the resultant perichondrocytes, cells in perichondrium-cartilage transition zone, and chondrocytes. Each type of cells was seeded in 35 mm easy grip cell culture dishes to give a density of 1200 cells/cm$^2$. Cells were cultured using Dulbecco's modified Eagle's medium and Ham's F-12 medium containing 10% fetal bovine serum and 1% antibiotic antimycotic solution in an incubator set at 37° C. under 5% $CO_2$. Starting 24 hours after the seeding, the medium was exchanged once in every 3 days. Cells reached confluency after culture for about 14 days. Then, cells were detached using 0.2% type II collagenase-containing Hank's balanced solution, followed by cell counting using a hemocytometer. Subsequently, the cells were seeded in 35 mm easy grip cell culture dishes to give a density of 1200 cells/cm$^2$. These operations were performed repeatedly. As a result of 14 passages over 182 days, it was revealed that perichondrocytes posses a growth capacity remarkably higher than that of cells in perichondrium-cartilage transition zone or chondrocytes (FIG. 14). In addition, it was revealed that cells in perichondrium-cartilage transition zone possess a remarkably higher than that of chondrocytes (FIG. 14).

*: $p<0.001$ (Mann Whitney U-Test with Bonferroni correction) n=5 (patient No.=5)

In Vitro Induction of Differentiation into Lipid and Bone

Induction of osteogenic and adipogenic differentiation of perichondrocytes and chondrocytes was performed for 3 weeks. As an osteogenic differentiation inducing medium, hMSC Osteogenic SingleQuots® was used. As an adipogenic differentiation inducing medium, hMSC Adipogenic Induction SingleQuots® was used. As a result, perichondrocytes formed lipid droplets and were stained with Oil red O, but chondrocytes did not form lipid droplets (FIG. 15A). Further, perichondrocytes showed a large number of Ca deposits and were stained with alizarin red, but chondrocytes showed no Ca deposits and were not stained with alizarin red (FIG. 15B).

In Vitro Induction of Differentiation into Cartilage

Differentiation into cartilage was induced by layered culture of perichondrocytes and chondrocytes. Each type of cells was adjusted to a density of $2.5 \times 10^4$ cells/cm$^2$ and seeded. After 7-day culture, cells were detached using 0.2% collagenase type II-containing Hank's balanced solution. The resultant cells were adjusted to a density of $2.5 \times 10^4$ cells/cm$^2$ and seeded over those cells that had been cultured for 7 days. Up to 48 hours after seeding, cells were cultured using Dulbecco's modified Eagle's medium and Ham's F-12 medium containing 10% fetal bovine serum and 1% antibiotic antimycotic solution. Starting 48 hours after seeding, cells were cultured using Dulbecco's modified Eagle's medium and Ham's F-12 medium containing 10% fetal bovine serum, 1% antibiotic antimycotic solution, L-ascorobic acid 2-phosphate, dexamethasone, insuline-like growth factor-1 and basic fibroblast growth factor. After 4-day culture using it, the medium was further seeded with cells at a density of $2.5 \times 10^4$ cells/cm$^2$, which were similarly cultured. These operations were repeated twice at an interval of 1 week. Culture was performed in an incubator set at 37° C. and under 5% $CO_2$ while exchanging the medium once in every 3 days. During these operations, histological examination was performed up to 3 weeks at intervals of 1 week. As a result, perichondrocytes were stained with Alcian blue and type II collagen on the cell culture dish in the same manner as chondrocytes (FIGS. 16A and 16B).

Histological Examination of Cartilage Tissues Regenerated In Vivo from Human Perichondrocytes and Chondrocytes Chondrocytes derived from perichondrocytes and chondrocytes that had been induced for differentiation into cartilage using a differentiation inducing medium were detached with a cell lifter. The detached cells were collected into a 2.5 ml syringe (Terumo, Japan) equipped with 23 G injection needle (Terumo, Japan). The cells in the syringe were injected subcutaneously in 1-ml portions into the dehaired back of severely immunodeficient mice (Sankyo, Japan) for transplant. One month and three months after the transplant, the resultant tissue was removed from each mouse and examined histologically. The removed tissue was stained with hematoxylin-eosin, Alcian blue, Elastica van Gieson, and type I and II collagen. As a result, both tissues derived from perichondrocytes and chondrocytes were stained with Alcian blue and Elastica van Gieson (see panels B, C, F and G in both FIGS. 17A and 17B). Further, the perichondrocytes-derived tissue was stained with type I and type II collagen (see panel D in both FIGS. 17A and 17B). On the other hand, the chondrocytes-derived tissue was stained with type II collagen but not with type I collagen (see panel H in both FIGS. 17A and 17B).

Cell Count Per $mm^2$ of In Vivo Reconstructed Cartilage

Cell counts were determined per $mm^2$ of the cartilage portion in the tissues removed one month and three months after transplant in the above-described "Histological Examination of Cartilage Tissues Regenerated in vivo from Human Perichondrocytes and Chondrocytes". While no change in cell count was observed in the perichondrocytes-derived tissue whether one month or three months passed after transplant, a decrease in cell count was observed in the chondrocytes-derived tissue three months after transplant (FIG. 18).

*: p<0.05,**: p<0.01 (Mann Whitney U-Test)

Method of Preparing Human Autoserum

Human autologous blood obtained from the same patient from whom cartilage had been collected was left to stand at room temperature for 20 min and then centrifuged at 3000 rpm for 10 min. The resultant supernatant was recovered as human autoserum. For the purpose of culture, a human autoserum immobilized at 37° C. for 30 min and then sterilized by filtration with a 0.45 µm filter was used.

Comparison of Colony Forming Activities in 10% Human Autoserum Medium Between Human Perichondrocytes, Cells in Perichondrium-Cartilage Transition Zone, and Chondrocytes Colony assay was performed on the resultant perichondrocytes, cells in perichondrium-cartilage transition zone, and chondrocytes. Each type of cells was seeded in 35 mm easy grip cell culture dishes at 500 cells/dish. Cells were cultured using Dulbecco's modified Eagle's medium and Ham's F-12 medium containing 10% human autoserum and 1% antibiotic antimycotic solution in an incubator set at 37° C. under 5% $CO_2$. Starting 24 hours after the seeding, the medium was exchanged once in every 7 days. After 9-day culture, formed colonies were photographed (FIG. 19). Human perichondrocytes formed larger colonies than human chondrocytes at day 9 of culture.

Microscopic Comparison of Human Perichondrocytes, Cells in Perichondrium-Cartilage Transition Zone and Chondrocytes after culture in 10% Human Autoserum Medium Each type of cells, i.e., the resultant perichondrocytes, cells in perichondrium-cartilage transition zone and chondrocytes was seeded in 24-well cell culture plates at 5000 cells/well. Cells were cultured using Dulbecco's modified Eagle's medium and Ham's F-12 medium containing 10% human autoserum and 1% antibiotic antimycotic solution in an incubator set at 37° C. under 5% $CO_2$. Starting 24 hours after the seeding, the medium was exchanged once in every 3 days. After 10 days of culture, formed colonies were photographed (FIG. 20). Each type of cells cultured in 10% human autoserum medium reached confluency more quickly than in 10% bovine serum medium.

All publications, patents and patent applications cited herein are incorporated herein by reference in their entirety.

INDUSTRIAL APPLICABILITY

According to the present invention, it has become possible to culture human chondrocytes by proliferating and differentiating human perichondrocytes. Further, it is possible to obtain a mass of human chondrocytes by culturing human perichondrocytes in centrifuge tubes, culturing such cells three dimensionally with collagen gel or the like, or culturing such cells in a layered form. The resultant cell mass may be transplanted either as it is or after being embedded in a cartilage treatment material such as collagen gel. Thus, such a cell mass is applicable to cartilage-related diseases (e.g., congenital auricular deformity, costicartilage defect, damage to articular cartilage such as knee osteoarthritis, tracheal cartilage defect, etc.). Further, the cell mass is also useful in treatment for aesthetic improvement in the field of cosmetic surgery, e.g., such as treatment for cartilage transplant in rhinoplasty, genioplasty, plastic surgery of small facial recesses, corrective surgery of facial left-right asymmetry, corrective surgery around eyelids, or cosmetic surgery of face.

SEQUENCE LISTING FREE TEXT

<SEQ ID NO: 1>
SEQ ID NO: 1 shows the nucleotide sequence of an RT-PCR forward primer for type I collagen.
<SEQ ID NO: 2>
SEQ ID NO: 2 shows the nucleotide sequence of an RT-PCR reverse primer for type I collagen.
<SEQ ID NO: 3>
SEQ ID NO: 3 shows the nucleotide sequence of an RT-PCR forward primer for type II collagen.
<SEQ ID NO: 4>
SEQ ID NO: 4 shows the nucleotide sequence of an RT-PCR reverse primer for type II collagen.
<SEQ ID NO: 5>
SEQ ID NO: 5 shows the nucleotide sequence of an RT-PCR forward primer for aggrecan.
<SEQ ID NO: 6>
SEQ ID NO: 6 shows the nucleotide sequence of an RT-PCR reverse primer for aggrecan.

The invention claimed is:

1. A method of preparing chondrocytes, comprising:
   separating an outermost layer and a fibroblast layer of human perichondrium away from a perichondrium-cartilage transition zone of the human perichondrium to produce a tissue section from the outermost layer and the fibroblast layer without the perichondrium-cartilage transition zone,
   then treating the tissue section from the outermost layer and the fibroblast layer with collagenase to produce an isolated perichondrocyte population, and
   then differentiating the perichondrocytes from the isolated perichondrocyte population from the tissue section from the outermost layer and the fibroblast layer into chondrocytes in a medium containing a serum and further containing an insulin-like growth factor and/or a basic fibroblast growth factor.

2. The method according to claim 1, wherein the serum is bovine serum.

3. The method according to claim 1, wherein the serum is an autoserum.

4. The method according to claim 1, wherein the isolated perichondrocyte population is differentiated into chondrocytes in the medium further containing DMEM/F 12, antibiotics and antimycotics.

5. The method according to claim 4, wherein the medium further contains dexamethasone and/or L-ascorbic acid.

6. A method of transplanting chondrocytes: comprising:
preparing the chondrocytes according to the method of claim 1; and
transplanting the chondrocytes and/or a cartilage tissue formed by said chondrocytes into a living body.

7. A method of preparing a matrix produced by chondrocytes, comprising
preparing the chondrocytes according to the method of claim 1; and
allowing said chondrocytes to produce the matrix.

8. The method according to claim 7, wherein the matrix is type II collagen and/or proteoglycan.

9. The method according to claim 1, wherein the medium contains the insulin-like growth factor.

10. The method according to claim 1, wherein the method further comprises proliferating the differentiated cell population.

11. A method of transplanting a cell derived from a human perichondrial tissue, comprising:
separating an outermost layer and a fibroblast layer of human perichondrium away from a perichondrium-cartilage transition zone of the human perichondrium to produce a tissue section from the outermost layer and the fibroblast layer without the perichondrium-cartilage transition zone,
then treating the tissue section from the outermost layer and the fibroblast layer with collagenase to produce an isolated perichondrocyte population;
then culturing the isolated perichondrocyte population in a centrifuge tube;
then proliferating and differentiating the perichondrocytes from the isolated perichondrocyte population into chondrocytes in a medium containing a serum and further containing an insulin-like growth factor and/or a basic fibroblast growth factor; and
then transplanting the chondrocytes or a cartilage tissue formed by the chondrocytes into a subject.

12. The method of transplanting a cell according to claim 11, wherein differentiating the cell into chondrocytes in the presence of the insulin-like growth factor and/or the basic fibroblast growth factor is accompanied by allowing said chondrocytes to produce a matrix.

13. The method according to claim 11, wherein the serum is bovine serum.

14. The method according to claim 11, wherein the serum is an autoserum.

15. The method according to claim 11, wherein the medium further contains DMEM/F 12, a serum, antibiotics, and antimycotics.

16. The method according to claim 11, wherein the medium further contains dexamethasone and/or L-ascorbic acid.

17. The method according to claim 11, wherein the medium contains the insulin-like growth factor.

18. The method according to claim 11, wherein the method comprises maintaining chondrogenic phenotype of the chondrocytes or the cartilage tissue formed by the chondrocytes for a month after the transplanting.

19. The method according to claim 11, wherein the method comprises maintaining cell count of the chondrocytes or the cartilage tissue formed by the chondrocytes for a month after the transplanting.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial
<220> FEATURE:
<223> OTHER INFORMATION: Primer

<400> SEQUENCE: 1
```

```
atgctcagct ttgtggatac gcgg                                          24

<210> SEQ ID NO 2
<211> LENGTH: 24
<212> TYPE: DNA
<213> ORGANISM: Artificial
<220> FEATURE:
<223> OTHER INFORMATION: Primer

<400> SEQUENCE: 2
aggaaagcca cgagcaccct gtgg                                          24

<210> SEQ ID NO 3
<211> LENGTH: 22
<212> TYPE: DNA
<213> ORGANISM: Artificial
<220> FEATURE:
<223> OTHER INFORMATION: Primer

<400> SEQUENCE: 3
catcattgac attgcaccca tg                                            22

<210> SEQ ID NO 4
<211> LENGTH: 22
<212> TYPE: DNA
<213> ORGANISM: Artificial
<220> FEATURE:
<223> OTHER INFORMATION: Primer

<400> SEQUENCE: 4
ttagtttcct gtctctgcct tg                                            22

<210> SEQ ID NO 5
<211> LENGTH: 24
<212> TYPE: DNA
<213> ORGANISM: Artificial
<220> FEATURE:
<223> OTHER INFORMATION: Primer

<400> SEQUENCE: 5
caggtgaaga ctttgtggac atcc                                          24

<210> SEQ ID NO 6
<211> LENGTH: 24
<212> TYPE: DNA
<213> ORGANISM: Artificial
<220> FEATURE:
<223> OTHER INFORMATION: Primer

<400> SEQUENCE: 6
cctcctcaaa ggtcagcgag tagc                                          24
```